US006908947B2

(12) United States Patent
Brendel et al.

(10) Patent No.: US 6,908,947 B2
(45) Date of Patent: Jun. 21, 2005

(54) SULFONAMIDE-SUBSTITUTED FUSED 7-MEMBERED RING COMPOUNDS, THEIR USE AS A MEDICAMENT, AND PHARMACEUTICAL PREPARATIONS COMPRISING THEM

(75) Inventors: Joachim Brendel, Bad Vilbel (DE); Hans Jochen Lang, Hofheim (DE); Uwe Gerlach, Hattersheim (DE)

(73) Assignee: Aventis Pharma Deutschland GmbH, Frankfurt Am Main (DE)

( * ) Notice: Subject to any disclaimer, the term of this patent is extended or adjusted under 35 U.S.C. 154(b) by 239 days.

(21) Appl. No.: 09/983,670

(22) Filed: Oct. 25, 2001

(65) Prior Publication Data

US 2002/0072514 A1 Jun. 13, 2002

Related U.S. Application Data

(63) Continuation of application No. 09/342,597, filed on Jun. 29, 1999, now Pat. No. 6,333,349, which is a continuation-in-part of application No. 09/028,452, filed on Feb. 24, 1998, now abandoned.

(30) Foreign Application Priority Data

Feb. 26, 1997 (DE) .......................... 197 07 656

(51) Int. Cl.[7] .......................... A61P 9/00; A61K 31/16; A61K 31/18; C07C 381/00; C07C 303/00
(52) U.S. Cl. ........................ 514/600; 514/601; 514/602; 514/603; 514/604; 514/605; 564/79; 564/80; 564/81; 564/82; 564/84; 564/85; 564/86; 564/87; 564/89; 564/90; 564/91; 564/92; 564/95; 564/96; 564/97; 564/98; 564/99
(58) Field of Search .............................. 564/79, 80, 81, 564/82, 84, 85, 86, 87, 89, 90, 91, 92, 95, 96, 97, 98, 99; 514/600, 601, 602, 603, 604, 605

(56) References Cited

U.S. PATENT DOCUMENTS

| 5,258,510 A | 11/1993 | Ogawa et al. ............ 540/476 |
| 6,333,337 B1 * | 12/2001 | Gross et al. ............... 514/307 |

FOREIGN PATENT DOCUMENTS

| EP | 0 370 901 A1 | 5/1990 |
| EP | 0 389 861 A1 | 10/1990 |
| WO | WO 94/13292 | 6/1994 |
| WO | WO 95/14470 | 6/1995 |

OTHER PUBLICATIONS

Derek R. Buckle et al., "Conformational and Steric Modifications of the Pyran Ring of the Potassium–Channel Activator Cromakalim," *J. Chem. Soc. Perkin Trans. 1*, pp. 2763–2771 (1991).

Colatsky, Thomas J. and Thomas M. Argentieri, "Potassium Channel Blockers as Antiarrhythmic Drugs," *Drug Development Research*, vol. 33, pp. 235–249 (1994).

Lohrmann, E. et al., "A new class of inhibitors of cAMP–medicated Cl⁻ secretion in rabbit colon, acting by the reduction of cAMP–activated K⁺ conductance," *Pflügers Archiv–European Journal of Physiology*, vol. 429, p. 517–530 (1995).

R. M. Soll et al., "N–Sulfonamides of Benzopyran–Related Potassium Channel Openers: Conversion of Glyburide Insensitive Smooth Muscle Relaxants to Potent Smooth Muscle Contractors," *Bioorganic & Medicinal Chemistry Letters*, vol. 4, No. 5, pp. 769–773 (1994).

\* cited by examiner

Primary Examiner—Brenda Coleman
(74) Attorney, Agent, or Firm—Joseph D. Rossi

(57) ABSTRACT

The present invention relates to compounds of formula I,

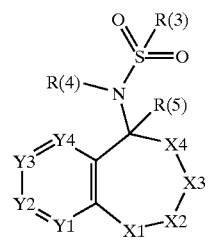

in which X1, X2, X3, X4, Y1, Y2, Y3, Y4, R(3), R(4) and R(5) have the meanings mentioned in the specification, their preparation and their use, in particular in pharmaceuticals. The compounds effect the potassium channel or the $I_{Ks}$ channel opened by cyclic adenosine monophosphate (cAMP) and are outstandingly suitable as pharmaceutical active compounds, for example for the prophylaxis and therapy of cardiovascular disorders, in particular arrhythmias, for the treatment of ulcers of the gastrointestinal region or for the treatment of diarrheal disorders.

14 Claims, No Drawings

SULFONAMIDE-SUBSTITUTED FUSED 7-MEMBERED RING COMPOUNDS, THEIR USE AS A MEDICAMENT, AND PHARMACEUTICAL PREPARATIONS COMPRISING THEM

CROSS REFERENCE TO RELATED APPLICATIONS

This is a continuation of application Ser. No. 09/342,597, filed Jun. 29, 1999 now U.S. Pat. No. 6,333,349, which is a continuation-in-part of application Ser. No. 09/028,452, filed Feb. 24, 1999 now abandoned, which claims priority of Federal Republic of Germany Patent Application No. 19707656.4, filed Feb. 26, 1997, all of which are incorporated herein by reference.

FIELD OF THE INVENTION

The present invention relates to compounds of formula I,

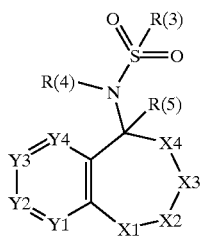

I in which X1, X2, X3, X4, Y1, Y2, Y3, Y4, R(3), R(4) and R(5) have the meanings indicated in the following, their preparation and their use, in particular in pharmaceuticals. The compounds affect the potassium channel opened by cyclic adenosine monophosphate (cAMP) or the $I_{K_s}$ channel and are outstandingly suitable as pharmaceutical active compounds, for example for the prophylaxis and therapy of cardiovascular disorders, in particular arrhythmias, for the treatment of ulcers of the gastrointestinal region or for the treatment of diarrheal disorders.

In pharmaceutical chemistry, in recent years the 4-acylaminochroman derivatives class and their homologs and analogs have been worked on intensively. The most prominent representative of this class is cromakalim of the formula A, an example of a homolog is the compound of the formula B (*J. Chem. Soc., Perkin Trans.* 1 (1991), 2763).

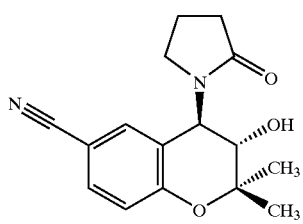

A

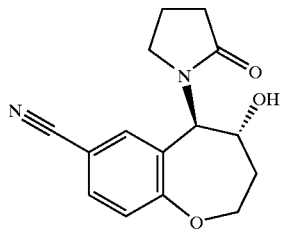

B

Cromakalim and other related 4-acylaminochroman derivatives are compounds having a relaxant action on smooth-muscular organs, such that they are used for lowering raised blood pressure as a result of vascular muscle relaxation and in the treatment of asthma as a result of the relaxation of the smooth musculature of the airways. It is common to all these preparations that they act at the cellular level, for example, of smooth muscle cells and lead there to opening of specific ATP-sensitive K⁺ channels. The increase in negative charge in the cell (hyperpolarization) induced by the efflux of K⁺ ions counteracts, via secondary mechanisms, the increase in the intracellular $Ca^{2+}$ concentration and thus cell activation, which leads, for example, to muscle contraction.

The compounds of formula I according to the invention differ structurally from these acylamino derivatives, in particular by the replacement of the acylamino group by a sulfonylamino function. While cromakalim (formula A) and the homologs of the formula B and analogous acylamino compounds act as openers of ATP-sensitive K⁺ channels, the compounds of formula I according to the invention having the sulfonylamino structure, however, do not show any opening action on this K⁺(ATP) channel, but surprisingly show a strong and specific blocking (closing) action on a K⁺ channel which is opened by cyclic adenosine monophosphate (cAMP) and differs fundamentally from the K⁺(ATP) channel mentioned. More recent investigations show that this K⁺(cAMP) channel identified in colonic tissue is very similar, perhaps even identical, to the $I^{K_s}$ channel identified in the cardiac muscle. In fact, it was possible for the compounds of formula I according to the invention to show a strong blocking action on the $I_{K_s}$ channel in guinea-pig cardiomyocytes and on the $I_{K_s}$ channel expressed in Xenopus oocytes. As a result of this blockage of the K⁺(cAMP) channel or of the $I_{K_s}$ channel, the compounds according to the invention display pharmacological actions of high therapeutic utility in the living body.

Beside the abovementioned cromakalim or acylaminochroman derivatives, compounds having 4-sulfonylaminochroman structure are also described in the literature which, however, differ markedly in structure or in biological action from the compounds of formula I according to the invention. Thus, EP-A-315 009 describes chroman derivatives having 4-phenylsulfonylamino structure, which are distinguished by antithrombotic and antiallergic properties. EP-A-389 861 and EP-A-370 901 describe 3-hydroxychroman derivatives having a 4-sulfonylamino group, which are described as K⁺(ATP) channel activators or have CNS actions. Further 4-sulfonylaminochroman derivatives are described in *Bioorg. Med. Chem. Lett.* 4 (1994), 769–773: "N-Sulfonamides of Benzopyran-Related Potassium Channel Openers: Conversion of Glyburyde Insensitive Smooth Muscle Relaxants to Potent Smooth Muscle Contractors".

The present invention relates to compounds of formula I

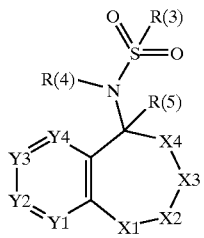

in which:
X1 is —O—, —S—, —SO—, —SO$_2$—, —CR(1)R(2)-, —NR(6)-, —CO— or —CR(1)R(7)-;
R(1) and R(2)
  independently of one another are hydrogen, CF$_3$, C$_2$F$_5$, C$_3$F$_7$, alkyl having 1, 2, 3, 4, 5 or 6 carbon atoms or phenyl,
    which is unsubstituted or is substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
R(1) and R(2)
  together are an alkylene chain having 2, 3, 4, 5, 6, 7, 8, 9 or 10 carbon atoms;
R(6) is hydrogen or —C$_n$H$_{2n}$—R(8),
  where a CH$_2$ group of the group C$_n$H$_{2n}$ can be replaced by —O—, —CH=CH—, —C≡C—, —CO—, —CO—O—, —O—CO—, —S—, —SO—, —SO$_2$—, —NR(9)- or —CONR(9)-;
    R(9) is hydrogen or alkyl having 1, 2 or 3 carbon atoms;
    n is zero, 1, 2, 3, 4, 5, 6, 7 or 8;
    R(8) is hydrogen, CF$_3$, C$_2$F$_5$, C$_3$F$_7$, cycloalkyl having 3, 4, 5, 6, 7 or 8 carbon atoms, dimethylamino, diethylamino, 1-piperidyl, 1-pyrrolidinyl, 4-morpholinyl, 4-methylpiperazin-1-yl, pyridyl, thienyl, imidazolyl or phenyl,
      where pyridyl, thienyl, imidazolyl and phenyl are unsubstituted or are substituted by 1 or 2 substituents, selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
X2 is —CR(1)R(2)- or —CR(2)R(10)-;
or
X2 if X3 and X1 are —CR(1)R(2)-, are also —O—, —S—, —SO—, —SO$_2$— or —NR(6)-,
  where the radicals R(1), R(2) and R(6) are defined as indicated for X1, but are independent of the meanings of the radicals in X1;
  R(10) together with R(7) is a bond;
  X3 is —CR(1)R(2)-;
or
X3 if X2 and X4 are —CR(1)R(2)-, are also —O—, —S—, —SO—, —SO$_2$— or—NR(6)-,
  where the radicals R(1), R(2) and R(6) are defined as indicated for X1, but are independent of the meanings of the radicals in X1;
X4 is —CR(1)R(2)-, —NR(6)-, —NR(11)-, —CH(OR(30))- or —CR(2)R(11)-,
  where the radicals R(1), R(2) and R(6) are defined as indicated for X1, but are independent of the meanings of the radicals in X1;
  R(30) is hydrogen, alkyl having 1, 2 or 3 carbon atoms or acyl having 1, 2, 3 or 4 carbon atoms;
  R(11) together with R(5) is a bond;
Y1, Y2, Y3 and Y4
  independently of one another are —CR(12)- or N,
    where at most 2 of the groups Y1, Y2, Y3 and Y4 can simultaneously be N;
  the radicals R(12)
    independently of one another are hydrogen, F, Cl, Br, I, alkyl having 1, 2, 3, 4 or 5 carbon atoms, cycloalkyl having 3, 4, 5, 6, 7 or 8 carbon atoms, CN, CF$_3$, C$_2$F$_5$, C$_3$F$_7$, N$_3$, NO$_2$, -Z-C$_m$H$_{2m}$—R(13) or phenyl, which is unsubstituted or is substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
    Z is —O—, —CO—, —CO—O—, —O—CO—, —S—, —SO—, SO$_2$—, —SO$_2$NR(14)-, —NR(14)- or —CONR(14)-;
      R(14) is hydrogen or alkyl having 1, 2 or 3 carbon atoms;
    m is zero, 1, 2, 3, 4, 5 or 6;
    R(13) is hydrogen, CF$_3$, C$_2$F$_5$, C$_3$F$_7$, cycloalkyl having 3, 4, 5, 6, 7 or 8 carbon atoms, —NR(15)R(16), —CONR(15)R(16), —OR(30a), phenyl, thienyl or an
    N-containing heterocycle having 1, 2, 3, 4, 5, 6, 7, 8 or 9 carbon atoms,
      where phenyl, thienyl and the N-containing heterocycle are unsubstituted or are substituted by 1 or 2 substituents selected from the group consisting of F, Cl, Br, I, CF$_3$, NO$_2$, CN, NH$_2$, OH, methyl, ethyl, methoxy, dimethylamino, sulfamoyl, methylsulfonyl and methylsulfonylamino;
    R(15) and R(16)
      independently of one another are hydrogen or alkyl having 1, 2 or 3 carbon atoms;
    or
    R(15) and R(16)
      together are a chain of 4 or 5 methylene groups, of which a CH$_2$ group can be replaced by —O—, —S—, —NH—, —N(CH$_3$)— or —N(benzyl)-;
    R(30a)
      is hydrogen, alkyl having 1, 2 or 3 carbon atoms or acyl having 1, 2, 3 or 4 carbon atoms;
or
Y1 and Y2
  together are a sulfur atom and Y3 and Y4 in each case are —CR(12)-; the radicals R(12)
    independently of one another are as defined for Y1, Y2, Y3, Y4;
R(3) is R(17)-C$_x$H$_{2x}$—NR(18)- or R(17)-C$_x$H$_{2x}$—,
  where a CH$_2$ group in the groups C$_x$H$_{2x}$ can be replaced by —O—, —CO—, —S—, —SO—, —SO$_2$— or —NR(19)-;
    R(19) is hydrogen, methyl or ethyl;
    R(17) is hydrogen, methyl, cycloalkyl having 3, 4, 5, 6, 7 or 8 carbon atoms, CF$_3$, C$_2$F$_5$ or C$_3$F$_7$;
    x is zero, 1, 2, 3, 4, 5, 6, 7, 8, 9 or 10;
    R(18) is hydrogen or alkyl having 1, 2, 3, 4, 5, 6, 7 or 8 carbon atoms;

or

R(18) and R(17)
    together are a bond if x is not smaller than 3;
or
R(3) is phenyl, which is unsubstituted or is substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
or
R(3) together with R(4)
    is an alkylene chain having 3, 4, 5, 6, 7, or 8 carbon atoms, where a $CH_2$ group of the alkylene chain can be replaced by —O—, —CO—, —S—, —SO— or $SO_2$—;
R(4) is —$C_rH_{2r}$—R(20),
    where a $CH_2$ group of the group $C_rH_{2r}$ can be replaced by —O—, —CH=CH—, —C≡C—, —CO—, —CO—O—, —O—CO—, —S—, —SO—, —$SO_2$—, —NR(21)- or —CONR(21)-;
    R(21) is hydrogen or alkyl having 1, 2 or 3 carbon atoms;
    r is zero, 1, 2, 3, 4, 5, 6, 7, 8, 9, 10, 11, 12, 13, 14, 15, 16, 17, 18, 19 or 20;
    R(20) is hydrogen, methyl, $CF_3$, $C_2F_5$, $C_3F_7$, cycloalkyl having 3, 4, 5, 6, 7 or 8 carbon atoms, —NR(22)R(23), phenyl, thienyl or an N-containing heterocycle having 1, 2, 3, 4, 5, 6, 7, 8 or 9 carbon atoms,
        where phenyl, thienyl and the N-containing heterocycle are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
    R(22) and R(23)
        independently of one another are hydrogen or alkyl having 1, 2 or 3 carbon atoms;
    or
    N-containing heterocycle having 1, 2, 3, 4, 5, 6, 7, 8 or 9 carbon atoms,
        where phenyl, thienyl and the N-containing heterocycle are unsubstituted or are substituted by 1 or 2
        substituents selected from the group consisting of F, Cl, Br, I, $CF_3$ $NO_2$, CN, $NH_2$, OH, methyl, ethyl, methoxy, dimethylamino, sulfamoyl, methylsulfonyl and methylsulfonylamino;
    R(22) and R(23)
        independently of one another are hydrogen or alkyl having 1, 2 or 3 carbon atoms;
    R(22) and R(23)
        together are a chain of 4 or 5 methylene groups, of which a $CH_2$ group can be replaced by —O—, —S—, —NH—, —$N(CH_3)$- or —N(benzyl)-;
R(5) is hydrogen or together with R(11) is a bond;
in all their stereoisomeric forms and mixtures thereof in any desired ratios, and also their physiologically tolerable salts.

Preferred compounds of formula I are those in which X1, X2, X3, X4, Y1, Y2, Y3, Y4, R(3), R(4) and R(5) have the meanings indicated above, but where one of the radicals R(3) and R(4), in particular the radical R(3), has a meaning other than hydrogen, and moreover compounds of formula I in which both radicals R(3) and R(4) have meanings other than hydrogen, in all their stereoisomeric forms and mixtures thereof in any desired ratios, and also their physiologically tolerable salts.

Particularly preferred compounds of formula I are those in which:
X1 is —O—, —S—, —SO—, —$SO_2$—, —CR(1)R(2)- or —NR(6)-;
R(1) and R(2)
    independently of one another are hydrogen, $CF_3$, $C_2F_5$, $C_3F_7$, alkyl having 1, 2, 3, 4, 5 or 6 carbon atoms or phenyl,
    which is unsubstituted or is substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
or
R(1) and R(2)
    together are an alkylene chain having 2, 3, 4, 5, 6, 7, 8, 9 or 10 carbon atoms;
R(6) is hydrogen or —$C_nH_{2n}$—R(8),
    where a $CH_2$ group of the group $C_nH_{2n}$ can be replaced by —O—, —CH=CH—, —C≡C—, —CO—, —CO—O—, —O—CO—, —S—, —SO—, —$SO_2$—, —NR(9)- or —CONR(9)-;
    R(9) is hydrogen or alkyl having 1, 2 or 3 carbon atoms;
    n is zero, 1, 2, 3, 4, 5, 6, 7 or 8;
    R(8) is hydrogen, $CF_3$, $C_2F_5$, $C_3F_7$, cycloalkyl having 3, 4, 5 or 6 carbon atoms, dimethylamino, diethylamino,
    1-piperidyl, 1-pyrrolidinyl, 4-morpholinyl,
    4-methylpiperazin-1-yl, pyridyl, thienyl, imidazolyl or phenyl,
        where pyridyl, thienyl, imidazolyl and phenyl are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
X2 is —CR(1)R(2)-;
where the radicals R(1) and R(2)
    are defined as indicated for X1, but are independent of the meanings of the radicals in X1;
X3 is —CR(1)R(2)-,
where the radicals R(1) and R(2)
    are defined as indicated for X1, but are independent of the meanings of the radicals in X1;
X4 is —CR(1)R(2)-, —NR(6)-, —NR(11)- or —CH(OR(30))-;
where the radicals R(1), R(2) and R(6)
    are defined as indicated for X1, but are independent of the meanings of the radicals in X1;
R(30) is hydrogen, alkyl having 1, 2 or 3 carbon atoms or acyl having 1, 2, 3 or 4 carbon atoms;
R(11) together with R(5), is a bond;
Y1, Y2, Y3 and Y4
    independently of one another are —CR(12)- or N,
        where at most 2 of the groups Y1, Y2, Y3 and Y4 can simultaneously be N;
    the radicals R(12)
        independently of one another are hydrogen, F, Cl, Br, I, alkyl having 1, 2, 3, 4 or 5 carbon atoms, cycloalkyl having 3, 4, 5 or 6 carbon atoms, CN, $CF_3$, $C_2F_5$, $C_3F_7$, $N_3$, $NO_2$, -Z-$C_mH_{2m}$—R(13) or phenyl,
            which is unsubstituted or is substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

Z is —O—, —CO—, —CO—O—, —O—CO—, —S—, —SO—, —$SO_2$—, —$SO_2$NR(14)-, —NR(14)- or —CONR(14)-;

R(14) is hydrogen or alkyl having 1, 2 or 3 carbon atoms;

m is zero, 1, 2, 3, 4, 5 or 6;

R(13) is hydrogen, $CF_3$, cycloalkyl having 3, 4, 5 or 6 carbon atoms, —NR(15)R(16), —CONR(15)R(16), —OR(30a), phenyl, thienyl or an N-containing heterocycle having 1, 2, 3, 4, 5, 6, 7, 8 or 9 carbon atoms, where phenyl, thienyl and the N-containing heterocycle are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(15) and R(16)
independently of one another are hydrogen or alkyl having 1, 2 or 3 carbon atoms;
or
R(15) and R(16)
together are a chain of 4 or 5 methylene groups, of which a $CH_2$ group can be replaced by —O—, —S—, —NH—, —N($CH_3$)- or —N(benzyl)-;

R(30a) is hydrogen, alkyl having 1, 2 or 3 carbon atoms or acyl having 1, 2, 3 or 4 carbon atoms;
or
Y1 and Y2
together are a sulfur atom and Y3 and Y4 in each case are —CR(12)-;

the radicals R(12)
independently of one another are defined as for Y1, Y2, Y3, Y4;

R(3) is R(17)-$C_xH_{2x}$—NR(18)- or R(17)-$C_xH_{2x}$—,
where a $CH_2$ group in the groups $C_xH_{2x}$ can be replaced by —O—, —CO—, —S—, —SO—, —$SO_2$— or —NR(19)-;

R(19) is hydrogen, methyl or ethyl;

R(17) is hydrogen, methyl, cycloalkyl having 3, 4, 5, 6, 7 or 8 carbon atoms, $CF_3$, $C_2F_5$, or $C_3F_7$;

x is zero, 1, 2, 3, 4, 5, 6, 7, 8, 9 or 10;

R(18) is hydrogen or alkyl having 1, 2, 3, 4, 5, 6, 7 or 8 carbon atoms;
or
R(18) and R(17)
together are a bond if x is not smaller than 3;
or
R(3) is phenyl,
which is unsubstituted or is substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
or
R(3) together with R(4)
is an alkylene chain having 3, 4, 5, 6, 7, or 8 carbon atoms, where a $CH_2$ group of the alkylene chain can be replaced by —O—, —CO—, —S—, —SO— or $SO_2$—;

R(4) is —$CH_{2r}$—R(20), where a $CH_2$ group of the group $C_rH_{2r}$ can be replaced by —O—, —CH=CH—, —C≡C—, —CO—, —CO—O—, —O—CO—, —S—, —SO—, —$SO_2$—, —NR(21)- or —CONR(21)-;

R(21) is hydrogen or alkyl having 1, 2 or 3 carbon atoms;

r is zero, 1, 2, 3, 4, 5, 6, 7, 8, 9, 10, 11, 12, 13, 14, 15, 16, 17, 18, 19 or 20;

R(20) is hydrogen, methyl, $CF_3$, $C_2F_5$, $C_3F_7$, cycloalkyl having 3, 4, 5 or 6 carbon atoms, —NR(22)R(23), phenyl, thienyl or an
N-containing heterocycle having 1, 2, 3, 4, 5, 6, 7, 8 or 9 carbon atoms, where phenyl, thienyl and the N-containing heterocycle are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

R(22) and R(23) independently of one another are hydrogen or alkyl having 1, 2 or 3 carbon atoms;
or
R(22) and R(23)
together are a chain of 4 or 5 methylene groups, of which a $CH_2$ group can be replaced by —O—, —S—, —NH—, —N($CH_3$)— or —N(benzyl)-;

R(5) is hydrogen or together with R(11) is a bond;

in all their stereoisomeric forms and mixtures thereof in any desired ratios, and also their physiologically tolerable salts.

Very particularly preferred compounds of formula I are those in which:

X1 is —O—, —S—, —SO—, —$SO_2$—, —CR(1)R(2)- or —NR(6)-;

R(1) and R(2)
independently of one another are hydrogen, $CF_3$, alkyl having 1, 2, 3, 4, 5 or 6 carbon atoms;
or
R(1) and R(2)
together are an alkylene chain having 2, 3, 4, 5 or 6 carbon atoms;

R(6) is hydrogen or —$C_nH_{2n}$—R(8),
where a $CH_2$ group of the group $C_nH_{2n}$ can be replaced by —O—, —CH=CH—, —C≡C—, —CO—, —CO—O—, —O—CO—, —S—, —SO—, —$SO_2$—, —NR(9)- or —CONR(9)-;

R(9) is hydrogen or alkyl having 1, 2 or 3 carbon atoms;

n is zero, 1, 2, 3, 4, 5, 6, 7 or 8;

R(8) is hydrogen, $CF_3$, cycloalkyl having 3, 4, 5 or 6 carbon atoms, dimethylamino, diethylamino, 1-piperidyl,
1-pyrrolidinyl, 4-morpholinyl, 4-methylpiperazin-1-yl, pyridyl, thienyl, imidazolyl or phenyl,
where pyridyl, thienyl, imidazolyl and phenyl are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;

X2 is —CR(1)R(2)-,
where the radicals R(1) and R(2)
are defined as indicated for X1, but are independent of the meanings of the radicals in X1;

X3 is —CR(1)R(2)-,
  where the radicals R(1) and R(2)
    are defined as indicated for X1, but are independent of the meanings of the radicals in X1;
X4 is —CR(1)R(2)-, —NR(6)-, —NR(11)- or —CH(OR(30))-;
  where the radicals R(1), R(2) and R(6)
    are defined as indicated for X1, but are independent of the meanings of the radicals in X1;
  R(30) is hydrogen, alkyl having 1, 2 or 3 carbon atoms or acyl having 1, 2, 3 or 4 carbon atoms;
  R(11) together with R(5) is a bond;
Y1, Y2, Y3 and Y4
  independently of one another are —CR(12)-;
  the radicals R(12)
    independently of one another are hydrogen, F, Cl, Br, I, alkyl having 1, 2, 3, 4 or 5 carbon atoms, cycloalkyl having 3, 4, 5 or 6 carbon atoms, CN, $CF_3$, $C_2F_5$, $C_3F_7$, $N_3$, $NO_2$, -Z-$C_mH_{2m}$—R(13) or phenyl,
      which is unsubstituted or is substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
    Z is —O—, —CO—, —CO—O—, —O—CO—, —S—, —SO—, —$SO_2$—, —$SO_2$NR(14)—, —NR(14)- or —CONR(14)-;
      R(14) is hydrogen or alkyl having 1, 2 or 3 carbon atoms;
    m is zero, 1, 2, 3, 4, 5 or 6;
    R(13) is hydrogen, $CF_3$, cycloalkyl having 3, 4, 5 or 6 carbon atoms, —NR(15)R(16), —CONR(15)R(16), —OR(30a), phenyl, thienyl or an N-containing heterocycle having 1, 2, 3, 4, 5, 6, 7, 8 or 9 carbon atoms,
      where phenyl, thienyl and the N-containing heterocycle are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
    R(15) and R(16)
      independently of one another are hydrogen or alkyl having 1, 2 or 3 carbon atoms;
    or
    R(15) and R(16)
      together are a chain of 4 or 5 methylene groups of which a $CH_2$ group can be replaced by —O—, —S—, —NH—, —N($CH_3$)— or —N(benzyl)-;
    R(30a)
      is hydrogen, alkyl having 1, 2 or 3 carbon atoms or acyl having 1, 2, 3 or 4 carbon atoms;
or
Y1 and Y2
  together are a sulfur atom and Y3 and Y4 are each —CR(12)-;
  the radicals R(12)
    independently of one another are as defined for Y1, Y2, Y3, Y4;
R(3) is R(17)-$C_xH_{2x}$—NR(18)- or R(17)-$C_xH_{2x}$—,
  where a $CH_2$ group in the groups $C_xH_{2x}$ can be replaced by —O—, —CO—, —S—, —SO—, —$SO_2$— or —NR(19)-;

R(19) is hydrogen, methyl or ethyl;
R(17) is methyl, cycloalkyl having 3, 4, 5 or 6 carbon atoms, $CF_3$, $C_2F_5$ or $C_3F_7$;
x is zero, 1, 2, 3, 4, 5, 6, 7, 8, 9 or 10;
R(18) is hydrogen or alkyl having 1, 2, 3, 4, 5, 6, 7 or 8 carbon atoms;
or
R(18) and R(17)
  together are a bond, if x is not smaller than 3;
or
R(3) is phenyl,
  which is unsubstituted or is substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
R(4) is —$C_rH_{2r}$—R(20),
  where a $CH_2$ group of the group $C_rH_{2r}$ can be replaced by —O—, —CH=CH—, —C≡C—, —CO—, —CO—O—, —O—CO—, —S—, —SO—, —$SO_2$—, —NR(21)- or —CONR(21)-;
    R(21) is hydrogen or alkyl having 1, 2 or 3 carbon atoms;
  r is zero, 1, 2, 3, 4, 5, 6, 7, 8, 9 or 10;
  R(20) is methyl, $CF_3$, $C_2F_5$, $C_3F_7$, cycloalkyl having 3, 4, 5 or 6 carbon atoms, —NR(22)R(23), phenyl, thienyl or an N-containing heterocycle having 1, 2, 3, 4, 5, 6, 7, 8 or 9 carbon atoms,
    where phenyl, thienyl and the N-containing heterocycle are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
  R(22) and R(23)
    independently of one another are hydrogen or alkyl having 1, 2 or 3 carbon atoms;
  or
  R(22) and R(23)
    together are a chain of 4 or 5 methylene groups, of which a $CH_2$ group can be replaced by —O—, —S—, —NH—, —N($CH_3$)- or —N(benzyl)-;
R(5) is hydrogen or together with R(11) is a bond;
in all their stereoisomeric forms and mixtures thereof in any desired ratios, and also their physiologically tolerable salts.

Especially preferred compounds of formula I are those in which:
X1 is —O— or —CR(1)R(2)-;
R(1) and R(2)
  independently of one another are hydrogen, $CF_3$, alkyl having 1, 2, 3, 4, 5 or 6 carbon atoms;
X2 is —CR(1)R(2)-,
  where the radicals R(1) and R(2)
    are defined as indicated for X1, but are independent of the meanings of the radicals in X1;
X3 is —CR(1)R(2)-,
  where the radicals R(1) and R(2)
    are defined as indicated for X1, but are independent of the meanings of the radicals in X1;
X4 is —CR(1)R(2)- or —CH(OR(30))-;
  where the radicals R(1) and R(2)
    are defined as indicated for X1, but are independent of the meanings of the radicals in X1;
  R(30) is hydrogen, alkyl having 1, 2 or 3 carbon atoms or acyl having 1, 2, 3 or 4 carbon atoms;

Y1, Y2, Y3 and Y4
  independently of one another are —CR(12)-;
  the radicals R(12)
    independently of one another are hydrogen, F, Cl, Br, I, alkyl having 1, 2, 3, 4 or 5 carbon atoms, CN, $CF_3$, $NO_2$, -Z-$C_mH_{2m}$—R(13) or phenyl,
      which is unsubstituted or is substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
    Z is —O—, —CO—, —CO—O—, —O—CO—, —S—, —SO—, —$SO_2$—, —$SO_2$NR(14)—, —NR(14)- or —CONR(14)-;
      R(14) is hydrogen or alkyl having 1, 2 or 3 carbon atoms;
    m is zero, 1, 2 or 3;
      R(13) is hydrogen, $CF_3$, —NR(15)R(16), —CONR(15)R(16), —OR(30a), phenyl, thienyl or an N-containing heterocycle having 1, 2, 3, 4, 5, 6, 7, 8 or 9 carbon atoms,
        where phenyl, thienyl or the N-containing heterocycle are unsubstituted or are substituted by 1 or 2 substituents selected from the group consisting of F, Cl, Br, I, $CF_3$, $NO_2$, CN, $NH_2$, OH, methyl, ethyl, methoxy, dimethylamino, sulfamoyl, methylsulfonyl and methylsulfonylamino;
    R(15) and R(16)
      independently of one another are hydrogen or alkyl having 1, 2 or 3 carbon atoms;
      or
    R(15) and R(16)
      together are a chain of 4 or 5 methylene groups, of which a $CH_2$ group can be replaced by —O—, —S—, —NH—, —N($CH_3$)- or —N(benzyl)-;
    R(30a)
      is hydrogen, alkyl having 1, 2 or 3 carbon atoms or acyl having 1, 2, 3 or 4 carbon atoms;
  R(3) is R(17)-$C_xH_{2x}$—,
    R(17) is methyl, cycloalkyl having 3, 4, 5 or 6 carbon atoms or $CF_3$;
    x is zero, 1, 2, 3, 4, 5, 6, 7, 8, 9 or 10;
  R(4) is —$C_rH_{2r}$—R(20),
    where a $CH_2$ group of the group $C_rH_{2r}$ can be replaced by —O—, —CO—O—, —O—CO—, —NR(21)- or —CONR(21)-;
    R(21) is hydrogen or alkyl having 1, 2 or 3 carbon atoms;
    r is zero, 1, 2, 3, 4, 5, 6, 7, 8, 9 or 10;
    R(20) is methyl, $CF_3$ or cycloalkyl having 3, 4, 5 or 6 carbon atoms;
  R(5) is hydrogen;
in all their stereoisomeric forms and mixtures thereof in any desired ratios, and also their physiologically tolerable salts.
  Particularly especially preferred compounds of formula I are those in which:
    X1 is —O— or —$CH_2$;
    X2 is —CR(1)R(2)-,
    R(1) and R(2)
      independently of one another are hydrogen or alkyl having 1, 2 or 3 carbon atoms;
    X3 is —$CH_2$— or —C($CH_3$)$_2$—;
    X4 is —$CH_2$— or —CHOH—;

Y1, Y2, Y3 and Y4
  independently of one another are —CR(12)-;
  the radicals R(12)
    independently of one another are hydrogen, F, Cl, Br, alkyl having 1, 2 or 3 carbon atoms, CN, $CF_3$, $NO_2$, -Z-$C_mH_{2m}$—R(13);
    Z is —O—, —CO—, —CO—O—, —O—CO—, —S—, —SO—, —$SO_2$—, —$SO_2$NR(14)-, —NR(14)- or —CONR(14)-;
      R(14) is hydrogen or alkyl having 1, 2 or 3 carbon atoms;
    m is zero, 1, 2 or 3;
      R(13) is hydrogen, $CF_3$, —NR(15)R(16), phenyl, piperidyl, 1-pyrrolidinyl, 4-morpholinyl, 4-methylpiperazin-1-yl, pyridyl, thienyl or imidazolyl;
    R(15) and R(16)
      independently of one another are hydrogen or alkyl having 1, 2 or 3 carbon atoms;
  R(3) is R(17)-$C_xH_{2x}$—,
    R(17) is methyl;
    x is zero, 1, 2 or 3;
  R(4) is —$CH_{2r}$—R(20),
    where a $CH_2$ group of the group $C_rH_{2r}$ can be replaced by —O—, —CO—O—, —O—CO—, —NR(21)- or —CONR(21)-;
    R(21) is hydrogen or alkyl having 1, 2 or 3 carbon atoms;
    r is zero, 1, 2, 3, 4, 5 or 6;
    R(20) is methyl, $CF_3$ or pyridyl;
  R(5) is hydrogen;
in all their stereoisomeric forms and mixtures thereof in any desired ratios, and also their physiologically tolerable salts.
  Very particularly especially preferred compounds of formula I are those in which:
    X1 is —O—;
    X2 is —CR(1)R(2)-,
    R(1) and R(2)
      independently of one another are hydrogen or alkyl having 1, 2 or 3 carbon atoms;
    X3 is —$CH_2$ or —C($CH_3$)$_2$—;
    X4 is —$CH_2$—;
    Y1 is CH;
    Y2 is CH;
    Y4 is CH;
    Y3 is —CR(12)-;
    R(12)
      is F, Cl, Br, alkyl having 1, 2 or 3 carbon atoms, CN, $CF_3$, $NO_2$, -Z-$C_mH_{2m}$—R(13);
      Z is —O—, —CO—, —CO—O—, —O—CO—, —S—, —SO—, —$SO_2$—, —$SO_2$NR(14)- or —CONR(14)-;
        R(14) is hydrogen or alkyl having 1, 2 or 3 carbon atoms;
      m is 1, 2 or 3;
      R(13) is hydrogen, $CF_3$, pyridyl or phenyl;
  R(3) is R(17)-$C_xH_{2x}$—,
    R(17) is methyl;
    x is zero, 1 or 2;
  R(4) is —$C_rH_{2r}$—R(20),
    where a $CH_2$ group of the group $C_rH_{2r}$ can be replaced by —O—, —CO—O—, —O—CO— or —CONR(21)-;

R(21) is hydrogen or alkyl having 1, 2 or 3 carbon atoms;

r is zero, 1, 2, 3, 4, 5 or 6;

R(20) is methyl or $CF_3$;

R(5) is hydrogen;

in all their stereoisomeric forms and mixtures thereof in any desired ratios, and also their physiologically tolerable salts.

Alkyl radicals and alkylene radicals can be straight-chain or branched. This also applies to the alkylene radicals of the formulae $C_nH_{2n}$, $C_mH_{2m}$, $C_xH_{2x}$ and $C_rH_{2r}$. Alkyl radicals and alkylene radicals can also be straight-chain or branched if they are substituted or are contained in other radicals, e.g. in an alkoxy radical or in an alkylmercapto radical or in a fluorinated alkyl radical. Examples of alkyl radicals are methyl, ethyl, n-propyl, isopropyl, n-butyl, isobutyl, sec-butyl, tert-butyl, n-pentyl, isopentyl, neopentyl, n-hexyl, 3,3-dimethylbutyl, heptyl, octyl, nonyl, decyl, undecyl, dodecyl, tridecyl, tetradecyl, pentadecyl, hexadecyl, heptadecyl, octadecyl, nonadecyl, or eicosyl. The bivalent radicals derived from these radicals, e.g. methylene, 1,1-ethylene, 1,2-ethylene, 1,1-propylene, 1,2-propylene, 2,2-propylene, 1,3-propylene, 1,4-butylene, 1,5-pentylene, 2,2-dimethyl-1,3-propylene, 1,6-hexylene, etc. are examples of alkylene radicals. Examples of acyl radicals are formyl, acetyl, propionyl, n-butyryl or isobutyryl.

N-containing heterocycles having 1, 2, 3, 4, 5, 6, 7, 8 or 9 carbon atoms are in particular the aromatic systems 1-, 2- or 3-pyrrolyl, 1-, 2-, 4- or 5-imidazolyl, 1-, 3-, 4- or 5-pyrazolyl, 1,2,3-triazol-1-, -4- or 5-yl, 1,2,4-triazol-1-, -3- or -5-yl, 1- or 5-tetrazolyl, 2-, 4- or 5-oxazolyl, 3-, 4-, or 5-isoxazolyl, 1,2,3-oxadiazol-4- or 5-yl, 1,2,4-oxadiazol-3- or 5-yl, 1,3,4-oxadiazol-2-yl or -5-yl, 2-, 4- or 5-thiazolyl, 3-, 4- or 5-isothiazolyl, 1,3,4-thiadiazol-2- or -5-yl, 1,2,4-thiadiazol-3- or -5-yl, 1,2,3-thiadiazol-4- or 5-yl, 2-, 3- or 4-pyridyl, 2-, 4-, 5- or 6-pyrimidinyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-indazolyl, 2-, 3-, 4-, 5-, 6- or 7-, 8-quinolyl, 1-, 3-, 4-, 5-, 6-, 7- or 8-isoquinolyl, 2-, 4-, 5-, 6-, 7- or 8-quinazolinyl, 3-, 4-, 5-, 6-, 7- or 8-cinnolinyl, 2-, 3-, 5-, 6-, 7- or 8-quinoxalinyl, 1-, 4-, 5-, 6-, 7- or 8-phthalazinyl.

Particularly preferred N-containing heterocycles are pyrrolyl, imidazolyl, quinolyl, pyrazolyl, pyridyl, pyrazinyl, pyrimidinyl and pyridazinyl.

Thienyl is either 2- or 3-thienyl.

Monosubstituted phenyl radicals can be substituted in the 2-, the 3- or the 4-position, disubstituted phenyl radicals in the 2,3-, 2,4-, 2,5-, 2,6-, 3,4- or 3,5-position. Correspondingly, the same also applies analogously to the N-containing heterocycles or the thiophene radical.

In the case of disubstitution of a radical, the substituents can be identical or different.

If the radicals R(1) and R(2) together are an alkylene chain, these radicals with the carbon atom carrying them form a ring which has a carbon atom in common with the 7-membered ring in the formula I; thus a spiro compound is then present. If R(7) and R(10) together are a bond, a double bond is present between the groups X1 and X2. Correspondingly, if R(5) and R(11) together are a bond, a double bond is present between the group X4 and the carbon atom which carries the radical R(3)-$SO_2$—NR(4)-. If R(17) and R(18) together are a bond, the group R(17)-$C_xH_{xn}$—NR(18)- is preferably a nitrogen heterocycle bonded via a nitrogen atom. If R(17) and R(18) together are a bond and the group R(17)-$C_xH_{2x}$—NR(18)- is a nitrogen heterocycle bonded via a nitrogen atom, this nitrogen heterocycle is preferably a 4-membered ring or a ring larger than a 4-membered ring, e.g. a 5-membered ring, 6-membered ring or 7-membered ring. If Y1 and Y2 together are a sulfur atom, the structural unit —Y2=Y1- is thus —S—, thus the 7-membered ring in the formula I is in this case fused to a thiophene ring.

If the compounds of formula I contain one or more acidic or basic groups or one or more basic heterocycles, the invention also relates to the corresponding physiologically or toxicologically tolerable salts, in particular the pharmaceutically utilizable salts. Thus the compounds of formula I which carry acidic groups, e.g. one or more COOH groups, can be used, for example, as alkali metal salts, preferably sodium or potassium salts, or as alkaline earth metal salts, e.g. calcium or magnesium salts, or as ammonium salts, e.g. as salts with ammonia or organic amines or amino acids. Compounds of formula I which contain one or more basic, i.e. protonatable, groups or contain one or more basic heterocyclic rings, can also be used in the form of their physiologically tolerable acid addition salts with inorganic or organic acids, for example as hydrochlorides, phosphates, sulfates, methanesulfonates, acetates, lactates, maleates, fumarates, malates, gluconates etc. If the compounds of formula I simultaneously contain acidic and basic groups in the molecule, in addition to the salt forms described, the invention also includes internal salts, so-called betaines. Salts can be obtained from the compounds of formula I by customary processes, for example by combination with an acid or base in a solvent or dispersant or alternatively from other salts by anion exchange.

When appropriately substituted, the compounds of formula I can be present in stereoisomeric forms. If the compounds of formula I contain one or more centers of asymmetry, these can independently of one another have the S configuration or the R configuration. The invention includes all possible stereoisomers, e.g. enantiomers or diastereomers, and mixtures of two or more stereoisomeric forms, e.g. enantiomers and/or diastereomers, in any desired ratios. The invention thus relates to enantiomers, for example, in enantiomerically pure form, both as levo- and dextrorotatory antipodes, and also in the form of mixtures of the two enantiomers in different ratios or in the form of racemates. If cis/trans isomerism is present, both the cis form and the trans form and mixtures of these forms are included in the invention. The preparation of individual stereoisomers can be carried out, if desired, by resolution of a mixture according to customary methods or, for example, by stereoselective synthesis. If mobile hydrogen atoms are present, the present invention also includes all tautomeric forms of the compounds of formula I.

The compounds of formula I can be prepared by different chemical processes. Thus, for example, a compound of formula I is obtained by a) reacting a compound of formula IIa or of formula IIb

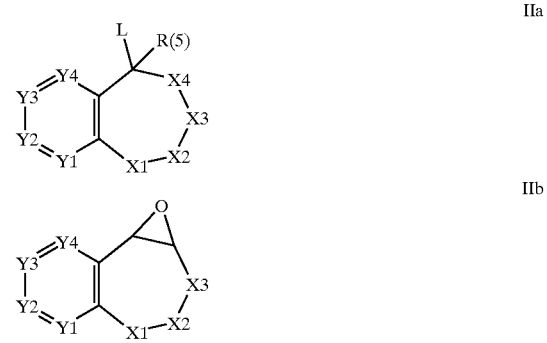

in which X1, X2, X3, X4, Y1, Y2, Y3, Y4 and R(5) have the meanings indicated above and L is a nucleofugic leaving group, in particular a customary nucleofugic leaving group such as, for example, F, Cl, Br, I, methanesulfonyloxy or p-toluenesulfonyloxy, in a manner known per se with a sulfonamide or its salts of formula III

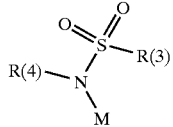

III in which R(3) and R(4) have the meanings indicated above and M is hydrogen or preferably a metal atom, particularly preferably lithium, sodium or potassium, or in the case of a reaction with a compound of formula IIb, also a trialkylsilyl radical, e.g. a trimethylsilyl radical;
or by
b) reacting a compound of formula IV

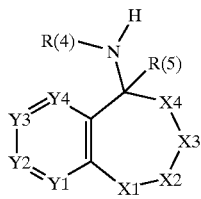

IV in which X1, X2, X3, X4, Y1, Y2, Y3, Y4, R(4) and R(5) have the meanings indicated above, with a sulfonic acid derivative of the formula V

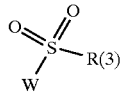

V in which R(3) has the meanings indicated above and W is a nucleofugic leaving group, such as, for example, fluorine, bromine, 1-imidazolyl, but in particular chlorine;
or by
c) reacting a compound of formula VI

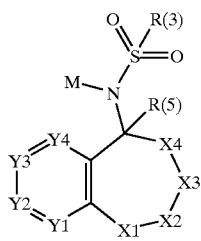

VI in which X1, X2, X3, X4, Y1, Y2, Y3, Y4, R(3), R(5) and M have the meanings indicated above, in a manner known per se in the sense of an alkylation reaction with an alkylating agent of formula VII:

R(4)-L  VII in which R(4) has the meanings indicated above with the exception of hydrogen and L has the meanings indicated above;

or by
d) carrying out, in a compound of formula I

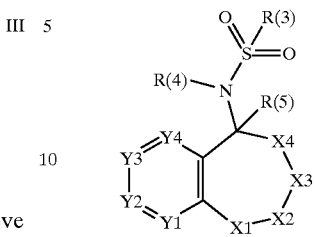

I in which X1, X2, X3, X4, Y1, Y2, Y3, Y4, R(3), R(4) and R(5) have the meanings indicated above, an electrophilic substitution reaction in at least one of the positions Y1 to Y4, provided a CH group is present in this position, or carrying out a chemical conversion, e.g. an alkylation or acylation, in at least one of the positions X1 to X4.

The procedure a) corresponds to the nucleophilic substitution of a leaving group in a reactive bicyclic system of formula IIa or IIb by a sulfonamide or one of its salts of formula III. Because of the higher nucleophilicity and higher reactivity of a sulfonamide present in the salt form, when using a free sulfonamide (formula III, M=H) it is preferred to generate a sulfonamide salt (formula III, M=metal cation) from this first by the action of a base. If a free sulfonamide (formula III, M=H) is employed, the deprotonation of the sulfonamide to the salt can be carried out in situ. Preferably, those bases are used which are not alkylated or only slightly alkylated themselves, such as, for example, sodium carbonate, potassium carbonate, sterically strongly hindered amines, e.g. dicyclohexylamine, N,N-dicyclohexylethylamine, or other strong nitrogen bases with low nucleophilicity, for example DBU (diazabicycloundecene), N,N',N'''-triisopropylguanidine etc. However, it is also possible to employ other customarily used bases for the reaction, such as potassium tert-butoxide, sodium methoxide, alkali metal hydrogencarbonates, alkali metal hydroxides, such as, for example LiOH, NaOH or KOH, or alkaline earth metal hydroxides, such as, for example $Ca(OH)_2$. In the case of a reaction of an epoxide of the formula IIb with a trialkyl- or trimethylsilylsulfonamide of formula III, it is advantageous to carry out the reaction in the presence of a fluoride, e.g. tetrabutylammonium fluoride.

The reaction is preferably carried out in a solvent, particularly preferably in polar organic solvents such as, for example, dimethylformamide (DMF), dimethylacetamide (DMA), dimethyl sulfoxide (DMSO), tetramethylurea (TMU), hexamethylphosphoramide (HMPT), tetrahydrofuran (THF), dimethoxyethane (DME) or other ethers, or, for example, alternatively in a hydrocarbon such as toluene or in a halogenated hydrocarbon such as chloroform or methylene chloride, etc. However, the reaction can also be carried out in polar protic solvents, such as, for example, in water, methanol, ethanol, isopropanol, ethylene glycol or its oligomers and their corresponding hemiethers or alternatively their ethers. The reaction can also be carried out in mixtures of these solvents. The reaction can equally be carried out, however, entirely without solvent. The reaction is preferably carried out in a temperature range from −10 to +140° C., particularly preferably in the range from 20 to 100° C. Favorably, procedure a) can also be carried out under the conditions of a phase-transfer catalysis.

The compounds of formula IIa are obtained by methods known from the literature, for example from the corresponding alcohols (formula IIa, L=OH, R(5)=H) by the action of a hydrogen halide of the formula HL (L=Cl, Br, I) or by the action of an inorganic acid halide (e.g. POCl₃, PCl₃, PCl₅, SOCl₂, SOBr₂), or, for example, by free-radical halogenation of the corresponding compounds of formula IIa where L=H and R(5)=H with elemental chlorine or bromine or with halogenating agents which can be activated by free radicals, such as, for example, N-bromosuccinimide (NBS) or sulfuryl chloride (SO₂Cl₂). In the case of free-radical halogenation, the reaction is in general carried out in the presence of a radical chain initiator such as energy-rich light of the visible or ultraviolet wave range or using a chemical free-radical initiator such as, for example, azodiisobutyronitrile.

The compounds of formula IIa, in which X4 is —NR(11)- and R(5) together with R(11) is a bond, are obtained, for example, from the corresponding lactams (formula IIa, L and R(5) are together a carbonyl oxygen atom, X4=NH) by the action of an inorganic acid halide (e.g. POCl₃, PCl₃, PCl₅, SOCl₂, SOBr₂).

The compounds of formula IIb are obtained by methods known from the literature, from the corresponding olefins of the formula IIc

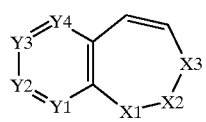

IIc in which X1, X2, X3, Y1, Y2, Y3 and Y4 have the meanings indicated above, e.g. by the action of a suitable inorganic or organic peroxide, such as, for example, H₂O₂ or m-chloroperbenzoic acid, or by base-catalyzed cyclization of the corresponding bromohydrin, which can be obtained from IIc, for example, by reaction with N-bromosuccinimide and water.

The epoxides of formula IIb can also be obtained in optically pure form from the olefins of the formula IIc by oxidation in the presence of the chiral Jacobsen catalyst, such as, for example, in *Tetrahedron Lett.* 32 (1991), 5055.

The procedure b) corresponds to the reaction, which is known per se and frequently used, of a reactive sulfonyl compound of formula V, in particular of a chlorosulfonyl compound (W=Cl), with an amino derivative of formula IV to give the corresponding sulfonamide derivative of formula I. The reaction can also be carried out without solvent, but reactions of this type are in most cases carried out using a solvent. The reaction is preferably carried out using a polar solvent, particularly preferably in the presence of a base, which itself can advantageously be used as a solvent, e.g. using triethylamine or in particular pyridine or its homologs. Suitable solvents are, for example, water, aliphatic alcohols, e.g. methanol, ethanol, isopropanol, sec-butanol, ethylene glycol, monoalkyl- and dialkyl ethers of monomeric and oligomeric ethylene glycol, tetrahydrofuran, dioxane, dialkylated amides such as DMF, DMA, and also TMU and HMPT. In this case, the reaction is in general carried out at a temperature from 0 to 160° C., preferably from 20 to 100° C.

The amines of formula IV are obtained in a manner known from the literature, preferably from the corresponding carbonyl compounds of formula VIII

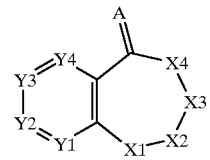

VIII in which X1, X2, X3, X4, Y1, Y2, Y3 and Y4 have the meanings indicated above and A is oxygen, either with ammonia or an amine of formula IX

R(4)-NH₂                        IX in which R(4) has the meanings indicated, under reductive conditions or reductive catalytic conditions, preferably at elevated temperature and in an autoclave. In this case, by condensation reaction of the ketones of formula VIII (A=oxygen) and of the amines of the formula IX in situ, Schiff bases of formula VIII in which a is R(4)-N= are primarily formed, which can be converted directly, i.e. without prior isolation, under reductive conditions into the amines of formula IV. However, the Schiff bases (formula VIII, A is R(4)-N=) intermediately formed, in the condensation reaction, from the compounds of formulae VIII and IX can be prepared by methods known from the literature and first isolated in order to then convert them in a separate step with a suitable reducing agent, such as, for example, NaBH₄, LiAlH₄, NaBH₃CN or by catalytic hydrogenation in the presence of, for example, Raney nickel or a noble metal such as, for example, palladium, into the compounds of formula IV.

The compounds of formula IV in which R(4) is hydrogen can advantageously also be obtained in a manner known from the literature by reduction of oximes or oxime ethers (formula VIII, A is =N—OR, R=H or alkyl) or hydrazones (formula VIII, A is =N—NR₂, R, for example =H or alkyl), e.g. using a complex metal hydride or by catalytic hydrogenation. The oximes and hydrazones necessary for this purpose are preferably prepared in a manner known per se from the ketones of formula VIII (A=oxygen) with hydrazine or one of its derivatives or, for example, with hydroxylamine hydrochloride under dehydrating conditions.

The procedure c) represents the alkylation reaction known per se of a sulfonamide or or of one of its salts (formula VI) with an alkylating agent (formula VII). Corresponding to the analogy of the reaction to procedure a), the reaction conditions already described in detail under procedure a) apply to procedure c).

The preparation of the sulfonamide derivatives of formula VI and their precursors has already been described in procedure b). The preparation of the alkylating agents of formula VII is carried out analogously to procedures in the literature or as described under procedure a), preferably from the corresponding hydroxy compounds (formula VII, L=hydroxyl).

The procedure d) corresponds to the further chemical conversion of compounds of formula I according to the invention into other compounds of formula I according to the invention, e.g. by electrophilic substitution reactions in one or in more of the positions marked by Y1 to Y4, if these are CH. Preferred substitution reactions are:

1. Aromatic nitration for the introduction of one or more nitro groups, which in subsequent reactions can in some cases or all be reduced to amino groups. The amino groups can in turn be converted into other groups in subsequent reactions, for example in a Sandmeyer reaction, e.g. for the introduction of cyano groups;

2. Aromatic halogenation, in particular for the introduction of chlorine, bromine or iodine;

3. Chlorosulfonation, e.g. by action of chlorosulfonic acid, for the introduction of a chlorosulfonyl group which can be converted into other groups in subsequent reactions, e.g. into a sulfonamido group;

4. The Friedel-Crafts acylation reaction for the introduction of an acyl radical or of a sulfonyl radical by action of the corresponding acid chlorides in the presence of a Lewis acid as a Friedel-Crafts catalyst, preferably in the presence of anhydrous aluminum chloride.

Further chemical conversions of compounds of formula I according to the invention which are possible are, for example, reactions in the positions X1 to X4. Thus, for example, compounds of formula I according to the invention (X4=CHOH) can be converted by alkylation or acylation with a compound of formula L-R(30), where L has the meanings indicated above and R(30) has the meanings indicated above with the exception of hydrogen, into the corresponding alkyl or acyl derivatives of formula I (X4=CHOR(30)). Furthermore, the hydroxyl group, for example, can be eliminated by dehydrating agents, such that a compound of formula I in which R(5) and (11) together form a bond is obtained.

In all procedures, it may be appropriate to temporarily protect functional groups in the molecule in certain reaction steps. Such protective group techniques are familiar to the person skilled in the art. The choice of a protective group for groups coming into consideration and the processes for their introduction and removal are described in the literature and can be adapted to the individual case, if appropriate, without difficulties.

The bicyclic precursors required for the above processes are either known from the literature or can be prepared analogously to known processes. Some methods for the preparation of these precursors are described, for example, in the following literature references, which in this regard are in full part of the present disclosure: J. Chem. Soc., Perkin Trans. 1, 1991, 2763; Eur. J. Med. Chem. 30 (1995), 377; Ind. J Chem. 9 (1971), 809; J. Heterocyclic Chem. 26 (1989), 1547.

It has already been said that the compounds of formula I surprisingly have a strong and specific blocking (closing) action on a $K^+$ channel which is opened by cyclic adenosine monophosphate (cAMP) and fundamentally differs from the well-known $K^+$(ATP) channel, and that this $K^+$(cAMP) channel identified in colonic tissue is very similar, perhaps even identical, to the $I_{Ks}$ channel identified in the cardiac muscle. For the compounds according to the invention, it was possible to show a strong blocking action on the $I_{Ks}$ channel in guinea-pig cardiomyocytes and in the $I_{sK}$ channel expressed in Xenopus oocytes. As a result of this blocking of the $K^+$(cAMP) channel or of the $I_{Ks}$ channel, the compounds according to the invention display pharmacological actions of high therapeutic utility in the living body and are outstandingly suitable as pharmaceutical active compounds for the therapy and prophylaxis of various syndromes.

Thus the compounds of formula I according to the invention are distinguished as a novel active compound class of potent inhibitors of stimulated gastric acid secretion. The compounds of formula I are thus valuable pharmaceutical active compounds for the therapy and prophylaxis of ulcers of the stomach and of the intestinal region, for example of the duodenum. They are also suitable, on account of their strong gastric secretion-inhibiting action, as excellent therapeutics for the therapy and prophylaxis of reflux esophagitis.

The compounds of formula I according to the invention are furthermore distinguished by an antidiarrheal action and are therefore suitable as pharmaceutical active compounds for the therapy and prophylaxis of diarrheal disorders.

The compounds of formula I according to the invention are furthermore suitable as pharmaceutical active compounds for the therapy and prophylaxis of cardiovascular disorders. In particular, they can be used for the therapy and prophylaxis of all types of arrhythmias, including atrial, ventricular and supraventricular arrhythmias, especially of cardiac arrhythmias which can be eliminated by action potential prolongation. They can be specifically used for the therapy and prophylaxis of atrial fibrillation and atrial flutter, and for the therapy and prophylaxis of reentry arrhythmias and for the prevention of sudden heart death as a result of ventricular fibrillation.

Although numerous substances having antiarrhythmics activity are already on the market, there is nevertheless no compound which is really satisfactory with respect to activity, range of application and side-effect profile, so that there is furthermore a need for the development of improved antiarrhythmics. The action of numerous known antiarrhythmics of the so-called class III is based on an increase in the myocardial refractory period by prolongation of the action potential duration. This is essentially determined by the extent or repolarizing $K^+$ streams which flow out of the cell via various $K^+$ channels. Particularly great importance is ascribed to the so-called "delayed rectifier" $I_K$, of which two subtypes exist, a rapidly activated $I_{Kr}$ and a slowly activated $I_{Ks}$. Most known class III antiarrhythmics block $I_{Kr}$ predominantly or exclusively (e.g. dofetilide, d-sotalol). It has been shown, however, that these compounds have an increased proarrhythmic risk at low or normal heart rates, arrhythmias which are designated as "torsades de pointes" in particular being observed (D. M. Roden; "Current Status of Class III Antiarrhythmic Drug Therapy"; Am. J. Cardiol. 72 (1993), 44B–49B). In the case of higher heart rates or stimulation of the β-receptors, however, the action potential-prolonging action of the $I_{Kr}$ blockers is markedly reduced, which is attributed to the fact that under these conditions the $I_{Ks}$ contributes more strongly to the repolarization. For these reasons, the substances according to the invention, which act as $I_{Ks}$ blockers, have significant advantages compared with the known $I_{Ks}$ blockers. It has now also been described that a correlation exists between $I_{Kr}$ channel inhibitory action and the suppression of life-threatening cardiac arrhythmias, such as are elicited, for example, by β-adrenergic hyper-stimulation (e.g. T. J. Colatsky, C. H. Follmer and C. F. Starmer; "Channel Specificity in Antiarrhythmic Drug Action; Mechanism of Potassium Channel Block and its Role in Suppressing and Aggravating Cardiac Arrhythmias"; Circulation 82 (1990), 2235–2242; A. E. Busch, K. Malloy, W. J. Groh, M. D. Varnum, J. P. Adelman and J. Maylie; "The Novel Class III Antiarrhythmics NE-10064 and NE-10133 Inhibit $I_{sK}$ Channels in Xenopus Oocytes and $I_{Ks}$ in Guinea Pig Cardiac Myocytes"; Biochem. Biophys. Res. Commun. 202 (1994), 265–270).

Moreover, the compounds of formula I contribute to a marked improvement of cardiac insufficiency, in particular of congestive heart failure, advantageously in combination with contraction-promoting (positively inotropic) active compounds, for example phosphodiesterase inhibitors.

In spite of the therapeutically utilizable advantages which can be achieved by a blockade of the $I_{Ks}$, hitherto only very few compounds have been described which inhibit this subtype of the "delayed rectifier". The substance azimilide which is in development admittedly also has a blocking action on the $I_{Ks}$, but mainly blocks the $I_{Kr}$ (selectivity 1:10).

WO-A-95/14470 claims the use of benzodiazepines as selective blockers of the $I_{Ks}$. Further $I_{Ks}$ blockers are described in *FEBS Letters* 396 (1996), 271–275: "Specific Blockade of Slowly Activating $I_{sK}$ Channels by Chromanols . . ." and *Pflügers Arch.—Eur. J. Physiol.* 429 (1995), 517–530: "A New Class of Inhibitors of cAMP-Mediated Cl⁻-Secretion in Rabbit Colon, Acting by the Reduction of cAMP-Activated K⁺ Conductance". The potency of the compounds mentioned there, however, is markedly lower than that of the compounds of formula I according to the invention.

The compounds of formula I according to the invention and their physiologically tolerable salts can thus be used in animals, preferably in mammals, and in particular in humans as pharmaceuticals per se, in mixtures with one another or in the form of pharmaceutical preparations. The present invention also relates to the compounds of formula I and their physiologically tolerable salts for use as pharmaceuticals, their use in the therapy and prophylaxis of the syndromes mentioned and their use for the production of medicaments therefor and of medicaments with K⁺ channel-blocking action. Furthermore, the present invention relates to pharmaceutical preparations which as active constituents contain an effective dose of at least one compound of formula I and/or of a physiologically tolerable salt thereof in addition to customary, pharmaceutically innocuous excipients and auxiliaries. The pharmaceutical preparations normally contain 0.1 to 90% by weight of the compounds of formula I and/or their physiologically tolerable salts. The pharmaceutical preparations can be prepared in a manner known per se. For this purpose, the compounds of formula I and/or their physiologically tolerable salts, together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain compounds of formula I according to the invention and/or their physiologically tolerable salts can be administered orally, parenterally, e.g. intravenously, rectally, by inhalation or topically, the preferred administration being dependent on the individual case, e.g. the particular course of the disorder to be treated.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, it is possible to use, for example, antioxidants, dispersants, emulsifiers, anti foams, flavor corrigents, preservatives, solubilizers, agents for achieving a depot effect, buffer substances or colorants.

The compounds of formula I can also be combined with other pharmaceutical active compounds to achieve an advantageous therapeutic effect. Thus in the treatment of cardiovascular disorders, advantageous combinations with substances having cardiovascular activity are possible. Possible combination components of this type which are advantageous for cardiovascular disorders are, for example, other antiarrhythmics, i.e. class I, class II or class III antiarrhythmics, such as, for example, $I_{Kr}$ channel blockers, e.g. dofetilide, or furthermore hypotensive substances such as ACE inhibitors (for example enalapril, captopril, ramipril), angiotensin antagonists, K⁺ channel activators, and also alpha- and beta-receptor blockers, but also sympathomimetic compounds and compounds having adrenergic activity, and also Na⁺/H⁺ exchange inhibitors, calcium channel antagonists, phosphodiesterase inhibitors and other substances having positively inotropic activity, such as, for example, digitalis glycosides, or diuretics. Combinations with substances having antibiotic activity and with antiulcer agents are furthermore advantageous, for example with H₂ antagonists (e.g. ranitidine, cimetidine, famotidine, etc.), in particular when used for the treatment of gastrointestinal disorders.

For an oral administration form, the active compounds are mixed with the additives suitable therefor, such as excipients, stabilizers or inert diluents, and brought by means of the customary methods into the suitable administration forms, such as tablets, coated tablets, hard capsules, aqueous, alcoholic or oily solutions. Inert carriers which can be used are, for example, gum arabic, magnesia, magnesium carbonate, potassium phosphate, lactose, glucose or starch, in particular corn starch. In this case the preparation can be carried out both as dry and as moist granules. Suitable oily excipients or solvents are, for example, vegetable or animal oils, such as sunflower oil or cod liver oil. Suitable solvents for aqueous or alcoholic solutions are, for example, water, ethanol or sugar solutions or mixtures thereof. Further auxiliaries, also for other administration forms are, for example, polyethylene glycols and polypropylene glycols.

For subcutaneous or intravenous administration, the active compounds, if desired with the substances customary therefor such as solubilizers, emulsifiers or further auxiliaries, are brought into solution, suspension or emulsion. The compounds of formula I and their physiologically tolerable salts can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the active compounds of formula I or their physiologically tolerable salts in a pharmaceutically acceptable solvent, such as, in particular, ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 10, in particular from approximately 0.3 to 3% by weight.

The dose of the active compound of formula I or of the physiologically tolerable salts thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the disease to be treated and on the sex, age, weight and individual responsiveness of the human or animal to be treated and on whether the therapy is acute or prophylactic. Customarily, the daily dose of a compound of formula I in the case of administration to a patient approximately 75 kg in weight is 0.001 mg/kg of bodyweight to 100 mg/kg of bodyweight, preferably 0.01 mg/kg of bodyweight to 20 mg/kg of bodyweight. The dose can be administered in the form of an individual dose or divided into several, e.g. two, three or four, individual doses. In particular in the treatment of acute cases of cardiac arrhythmias, for example in an intensive care unit, parenteral administration by injection or infusion, e.g. by an intravenous continuous infusion, can also be advantageous.

The compounds of formula I and their physiologically tolerable salts selectively inhibit K+(cAMP) channels and $I_{Ks}$ channels. On account of this property, apart from use as pharmaceutical active compounds in human medicine and veterinary medicine, they can also be employed as a scientific tool or as aids for biochemical investigations in which an effect on potassium channels is intended, and also for diagnostic purposes, e.g. in the in vitro diagnosis of cell or tissue samples. They can further be employed, as already mentioned above, as intermediates for the preparation of other pharmaceutical active compounds.

EXPERIMENTAL SECTION

List of Abbreviations

| | |
|---|---|
| DMA | N,N-Dimethylacetamide |
| DMSO | Dimethyl sulfoxide |
| EA | Ethyl acetate |
| m.p. | Melting point (If not stated otherwise, the melting points of the unpurified crude products are indicated; the melting points of the respective pure substances can be quite markedly higher.) |
| NBS | N-Bromosuccinimide |
| RT | Room temperature |
| THF | Tetrahydrofuran |

EXAMPLE 1

3-Fluoro-5-(N-ethylsulfonylamino)-6,7,8,9-tetrahydro-5H-benzocycloheptene

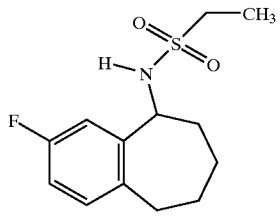

a) 5 g (28 mmol) of 8-fluoro-1-benzosuberone and 2.1 g (31 mmol) of hydroxylamine hydrochloride were heated under reflux for 5 h in 20 ml of ethanol and 20 ml of pyridine. After distilling off the solvents on a rotary evaporator, the residue was treated with water, adjusted to pH 2 using dil. hydrochloric acid and stirred until the initially oily product crystallized. 5.1 g of 8-fluoro-1-benzosuberone oxime (m.p. 97–103° C.) were obtained, which was reduced to 3-fluoro-5-amino-6,7,8,9-tetrahydro-5H-benzocycloheptene by hydrogenation in methanol at normal pressure and RT using Raney nickel as a catalyst. Yield: 4.3 g; m.p. of the hydrochloride 212–216° C.

b) 2.3 g (18 mmol) of ethanesulfonyl chloride were added dropwise with ice-cooling to a solution of 2.68 g (15 mmol) of 3-fluoro-5-amino-6,7,8,9-tetrahydro-5H-benzocycloheptene and 1.5 g (60 mmol triethylamine in 40 ml of THF. The mixture was allowed to come to room temperature and was stirred overnight, and the solvent was distilled off in vacuo. After stirring the residue with water, the precipitated product was filtered off with suction. 2.9 g of 3-fluoro-5-(N-ethylsulfonylamino)-6,7,8,9-tetrahydro-5H-benzocycloheptene were obtained, m.p. 118–121° C.

EXAMPLE 2

3-Fluoro-5-(N-ethylsulfonyl-N-methylamino)-6,7,8,9-tetrahydro-5H-benzocycloheptene

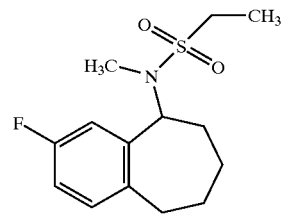

A solution of 0.81 g (3 mmol) of 3-fluoro-5-(N-ethylsulfonylamino)-6,7,8,9-tetrahydro-5H-benzocyclohepte (Example 1) in 10 ml of DMA was added dropwise under argon to a suspension of 0.12 g (4.1 mmol) of 80 percent sodium hydride in 5 ml of DMA. After stirring at RT for 3 h, 0.63 g (4.5 mmol) of methyliodide was added dropwise and the mixture was stirred overnight at RT. After distilling off the solvent, the residue was treated with water and extracted with EA. The organic phase was concentrated in vacuo after drying over sodium sulfate. 0.64 g of 3-fluoro-5-(N-ethylsulfonyl-N-methylamino)-6,7,8,9-tetrahydro-5H-benzocycloheptene was obtained.

EXAMPLE 3

3-Fluoro-5-(N-ethylsulfonyl-N-butylamino)-6,7,8,9-tetrahydro-5H-benzocycloheptene

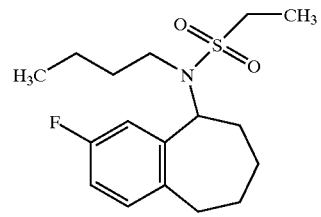

From 0.12 g (4.1 mmol) of 80 percent sodium hydride, 0.81 g (3 mmol) of 3-fluoro-5-(N-ethylsulfonylamino)-6,7,8,9-tetrahydro-5H-benzocycloheptene and 0.82 g (4.5 mmol) of butyliodide, 0.88 g of 3-fluoro-5-(N-ethylsulfonyl-N-butylamino)-6,7,8,9-tetrahydro-5H-benzocycloheptene was obtained analogously to Example 2.

EXAMPLE 4 trans-7-Nitro-5-(N-ethylsulfonyl-N-methylamino)-2,3,4,5-tetrahydro-1-benzoxepin-4-ol

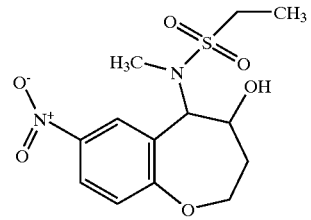

a) 2,3-Dihydro-7-nitro-1-benzoxepine
10.2 g of sodium borohydride were added in portions at 0° C. with vigorous stirring to a suspension of 50 g of 3,4-dihydro-7-nitro-1-benzoxepin-5(2H)-one (*J. Chem. Soc., Perkin Trans.* 1 (1991), 2763) in 345 ml of methanol. After 30 min, the reaction mixture was added to ice water, the solid was filtered off with suction and 43 g of 7-nitro-2,3,4,5-tetrahydro-1-benzoxepin-5-ol was obtained. This was heated on a water separator for 2 h with 1 g of p-toluenesulfonic acid in 520 ml of toluene. After cooling, the organic phase was washed with sodium bicarbonate solution and sodium chloride solution. After drying over sodium sulfate and concentrating, 38.8 g of 2,3-dihydro-7-nitro-1-benzoxepine were obtained, m.p. 98–100° C.

b) 4,5-Epoxy-7-nitro-2,3,4,5-tetrahydro-1-benzoxepine 72.3 g of NBS were added in one portion with ice-cooling to a solution of 38.8 g of 2,3-dihydro-7-nitro-1-benzoxepine in 780 ml of DMSO and 78 ml of water, the temperature rising to 30° C. After stirring at RT for 90 min, the reaction mixture was poured into 5 L of ice water and stirred for 1 h, the crystalline precipitate was filtered off with suction and 60 g of the bromohydrin were obtained. A solution of this bromohydrin in 465 ml of methanol was added dropwise at RT to a solution of 5.1 g of sodium in 400 ml of methanol. After stirring for 1 h, the deposited precipitate was filtered off with suction and washed with water. After drying, 37 g of 4,5-epoxy-7-nitro-2,3,4,5-tetrahydro-1-benzoxepine were obtained, m.p. 123–125° C.

c) N-Methyl-N-trimethylsilylethanesulfonamide

A mixture of 33 g of N-methylethanesulfonamide, 101 g of hexamethyldisilazane and a spatula tipful of ammonium chloride was heated under argon, first for 2 h at 100° C. and then for a further 1 h at 130° C. By distillation of the reaction mixture in vacuo, 42 g of N-methyl-N-trimethylsilylethanesulfonamide were obtained with the boiling point 118–121° C./10 mm Hg.

d) trans-7-Nitro-5-(N-ethylsulfonyl-N-methylamino)-2,3,4,5-tetrahydro-1-benzoxepin-4-ol 2 g of tetrabutylammonium fluoride were added with stirring to a mixture of 6 g of 4,5-epoxy-7-nitro-2,3,4,5-tetrahydro-1-benzoxepine and 9.5 g of N-methyl-N-trimethylsilylethanesulfonamide. The reaction mixture was then heated for 3 h at 65° C., stirred overnight at RT and poured onto ammonium chloride solution. It was extracted several times with EA, and the organic phase was washed with water and dried over sodium sulfate. After concentration and recrystallization of the solid residue from isopropanol, 7.1 g of trans-7-nitro-5-(N-ethylsulfonyl-N-methylamino)-2,3,4,5-tetrahydro-1-benzoxepin-4-ol were obtained, m.p. 133–135° C.

EXAMPLE 5 trans-7-Cyano-5-(N-ethylsulfonyl-N-methylamino)-2,3,4,5-tetrahydro-1-benzoxepin-4-ol

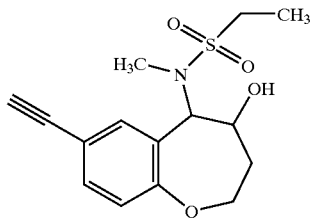

1.5 g of tetrabutylammonium fluoride were added with stirring to a mixture of 4 g of 4,5-epoxy-2,3,4,5-tetrahydro-1-benzoxepine-7-carbonitrile (*J. Chem. Soc., Perkin Trans.* 1 (1991), 2763) and 7.0 g of N-methyl-N-trimethylsilylethanesulfonamide. The reaction mixture was then heated for 3 h at 60° C., stirred overnight at RT and poured onto ammonium chloride solution. It was extracted several times with EA, and the organic phase was washed with water and dried over sodium sulfate. After concentration and recrystallization of the solid residue from cyclohexane/EA (1:5), 3.2 g of trans-7-cyano-5-(N-ethylsulfonyl-N-methylamino)-2,3,4,5-tetrahydro-1-benzoxepin-4-ol were obtained, m.p. 142–144° C.

EXAMPLE 6

5-(N-Ethylsulfonyl-N-methylamino)-2,3,4,5-tetrahydro-1-benzoxepine

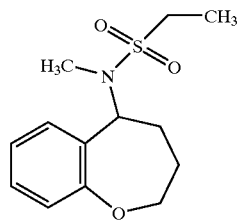

a) A solution of 10.0 g (62 mmol) of 3,4-dihydro-1-benzoxepin-5(2H)-one (*J. Chem. Soc., Perkin Trans.* 1 (1991), 2763) and 4.63 g (68 mmol) of hydroxylamine hydrochloride in 45 ml of ethanol and 45 ml of pyridine was heated under reflux for 5 h. After distilling off the solvents on a rotary evaporator, the residue was treated with water, adjusted to pH 2 with dil hydrochloric acid and stirred for 3 h. After filtering off the precipitated product with suction and drying it, 10.2 g of 3,4-dihydro-1-benzoxepin-5(2H)-one oxime were obtained, m.p. 96–98° C.

b) A solution of 2.0 g (11.3 mmol) of 3,4-dihydro-1-benzoxepin-5(2H)-one oxime in 15 ml of 1,2-dimethoxyethane (DME) was added dropwise at 0° C. under argon to a mixture of 4.5 g (23.7 mmol) of titanium tetrachloride and 1.79 g (47.4 mmol) of sodium borohydride in 50 ml of DME over the course of 20 min. After stirring at RT for 2 days, 100 ml of water were added dropwise and the mixture was rendered alkaline using conc. ammonia solution. After filtering off the precipitate with suction, the filtrate was extracted three times with EA. After washing with sodium chloride solution, drying over magnesium sulfate and concentrating, 2.1 g of 5-amino-2,3,4,5-tetrahydro-1-benzoxepine were obtained.

c) 0.86 g (6.7 mmol) of ethanesulfonyl chloride was added dropwise with ice cooling to a solution of 1.0 g (6.1 mmol) of 5-amino-2,3,4,5-tetrahydro-1-benzoxepine and 2.5 g (24 mmol) of triethylamine in 20 ml of THF. The mixture was allowed to come to room temperature and was stirred overnight, and the solvent was distilled off in vacuo. After stirring the residue with water, the deposited product was filtered off with suction. 1.1 g of 5-ethylsulfonylamino-2,3,4,5-tetrahydro-1-berzoxepine were obtained, m.p. 109–111° C.

d) A solution of 1.0 g (3.9 mmol) of 5-ethylsulfonylamino-2,3,4,5-tetrahydro-1-benzoxepine in 15 ml of THF were added dropwise under nitrogen to a suspension of 0.16 g (5.4 mmol) of 80 percent sodium hydride in 10 ml of THF. After stirring at RT for 3 h, 1.6 g (11 mmol) of methyl iodide were added dropwise and the mixture was additionally stirred overnight at RT. After distilling off the solvent, the residue was treated with water and extracted with EA. The organic phase was concentrated in vacuo after drying over sodium sulfate. 1.0 g of 5-(N-ethylsulfonyl-N-methylamino)-2,3,4,5-tetrahydro-1-benzoxepine was obtained, m.p. 122–124° C.

EXAMPLE 7

5-(N-Butyl-N-ethylsulfonylamino)-2,3,4,5-tetrahydro-1-benzoxepine

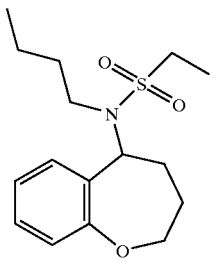

From 7.1 g of 5-ethylsulfonylamino-2,3,4,5-tetrahydro-1-benzoxepine (Example 6c), 8.3 g of 5-(N-butyl-N-ethylsulfonylamino)-2,3,4,5-tetrahydro-1-benzoxepine were obtained by alkylation with butyl iodide analogously to Example 11 as a viscous oil which crystallized after a relatively long time, m.p. 62–65° C.

EXAMPLE 8

5-(N-Methyl-N-methylsulfonylamino)-2,3,4,5-tetrahydro-1-benzoxepine

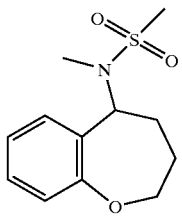

a) 1.54 g (13.4 mmol) of methanesulfonyl chloride were added dropwise with ice cooling to a solution of 2.0 g (12.2 mmol) of 5-amino-2,3,4,5-tetrahydro-1-benzoxepine (Example 6b) and 3.7 g (36.6 mmol triethylamine in 40 ml of THF. The mixture was allowed to come to RT and was stirred overnight and treated with 50 ml of water, and the THF was distilled off in vacuo. The residue was diluted with a further 50 ml of water and stirred for 3 h, and the deposited product was filtered off with suction. After drying in vacuo, 2.2 g of 5-methylsulfonylamino-2,3,4,5-tetrahydro-1-benzoxepine were obtained, m.p. 105–106° C.

b) A solution of 1.1 g (6.2 mmol) of 5-methylsulfonylamino-2,3,4,5-tetrahydro-1-benzoxepine in 15 ml of THF was added dropwise to a suspension of 0.23 g (6.2 mmol) of 80 percent sodium hydride in 10 ml of THF. After 2 h at RT, 0.94 g (6.7 mmol) of iodomethane were added and the mixture was stirred overnight at RT. After distilling off the solvent in vacuo, the residue was taken up in EA, and the solution was washed with dilute hydrochloric acid and water, dried over magnesium sulfate and concentrated. Subsequent recrystallization of the product from isopropanol yielded 0.5 g of 5-(N-methyl-N-methylsulfonylamino)-2,3,4,5-tetrahydro-1-benzoxepine, m.p. 143–145° C.

EXAMPLE 9

5-(N-Butyl-N-methylsulfonylamino)-2,3,4,5-tetrahydro-1-benzoxepine

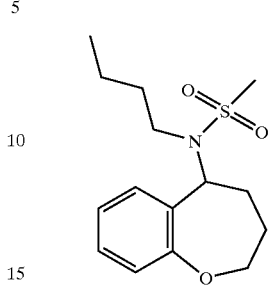

1.0 g of 5-methylsulfonylamino-2,3,4,5-tetrahydro-1-benzoxepine (Example 8a) were reacted with sodium hydride and iodobutane in DMF analogously to Example 11. After recrystallization of the crude product (1.0 g) from isopropanol, 0.4 g of 5-(N-butyl-N-methylsulfonylamino)-2,3,4,5-tetrahydro-1-benzoxepine was obtained, m.p. 78–79° C.

EXAMPLE 10

7-Chloro-9-methyl-5-(N-ethylsulfonyl-N-methylamino)-2,3,4,5-tetrahydro-1-benzoxepine

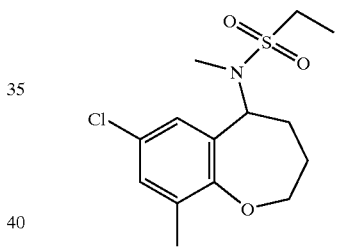

a) A mixture of 90 g of 4-(4-chloro-2-methylphenoxy)butyric acid (Aldrich) and 1000 g of polyphosphoric acid was stirred for 4.5 h at 85° C. The batch was then poured onto 5 L of ice water, stirred for 1 h and extracted with ether. The combined organic phases were washed several times with sodium carbonate solution and water, dried over magnesium sulfate and concentrated in a rotary evaporator. The dark residue was then taken up in ether again and boiled several times with active carbon and silica gel, and filtered until the solution was only slightly colored. After concentrating, 48.4 g of 7-chloro-9-methyl-3,4-dihydro-2H-1-benzoxepin-5-one were obtained, m.p. 56–58° C.

b) 3.0 g of 7-chloro-9-methyl-3,4-dihydro-2H-1-benzoxepin-5-one, 50 ml of anhydrous methanol, 10.9 g of ammonium acetate and 0.63 g of sodium cyanoborohydride were stirred for 5 h at 60° C. and then for 2 days at RT. The reaction mixture was then acidified with hydrochloric acid and then concentrated on a rotary evaporator. The residue was taken up in water, and the solution was rendered alkaline with ammonia solution and extracted with EA. After drying and concentrating, the product was purified by chromatography on silica gel using ethyl acetate/methanol 9:1 and 1.3 g of 5-amino-7-chloro-9-methyl-2,3,4,5-tetrahydro-1-benzoxepine were obtained.

c) 0.86 g of ethanesulfonyl chloride was added dropwise with ice-cooling to a solution of 1.3 g of 5-amino-7-chloro-9-methyl-2,3,4,5-tetrahydro-1-benzoxepine and 2.4 g of triethylamine in 30 ml of THF. The mixture was allowed to come to room temperature and was stirred overnight, and the solvent was distilled off in vacuo. After stirring the residue with water, the deposited product was filtered off with suction and dried in vacuo. 1.6 g of 7-chloro-9-methyl-5-(N-ethylsulfonylamino)-2,3,4,5-tetrahydro-1-benzoxepine were obtained, m.p. 144–145° C. psd) A solution of 0.6 g (2.0 mmol) of 7-chloro-9-methyl-5-(N-ethylsulfonylamino)-2,3,4,5-tetrahydro-1-benzoxepine in 8 ml of THF was added dropwise under nitrogen to a suspension of 0.1 g (2.7 mmol) of 80 percent sodium hydride in 5 ml of THF. After stirring at RT for 1 h, 0.41 g (2.9 mmol) of methyl iodide was added dropwise and the mixture was additionally stirred overnight at RT. After distilling off the solvent, the residue was treated with water and extracted with EA. After washing the organic phase with dil. hydrochloric acid and water, and drying over magnesium sulfate, it was concentrated in vacuo and the crude product was recrystallized from methylene chloride. 0.4 g of 7-chloro-9-methyl-5-(N-ethylsulfonyl-N-methylamino)-2,3,4,5-tetrahydro-1-benzoxepine was obtained, m.p. 141–143° C. $^1$H-NMR (CDCl$_3$): δ (ppm)=1.35 (3H), 1.9–2.2 (4H), 2.2 (3H), 2.9 (3H), 3.05 (2H), 3.7 (1H), 4.2 (1H), 5.15 (1H), 7.1 (2H).

EXAMPLE 11

5-(N-Butyl-N-ethylsulfonylamino)-7-chloro-9-methyl-2,3,4,5-tetrahydro-1-benzoxepine

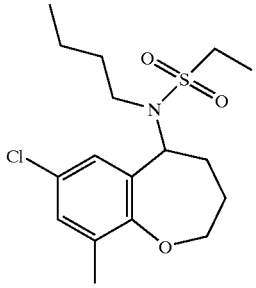

A solution of 0.8 g (2.6 mmol) of 7-chloro-9-methyl-5-(N-ethylsulfonylamino)-2,3,4,5-tetrahydro-1-benzoxepine (Example 10c) in 10 ml of DMF was added dropwise under nitrogen to a suspension of 0.1 g (2.7 mmol) of 80 percent sodium hydride in 8 ml of DMF. After stirring at RT for 30 min, 0.68 g (3.7 mmol) of butyl iodide was added dropwise and the mixture was additionally stirred overnight at RT. After distilling off the solvent, the residue was treated with water and extracted with EA. After washing the organic phase with dil. hydrochloric acid in water, and drying over magnesium sulfate, it was concentrated in vacuo. 0.9 g of 5-(N-butyl-N-ethylsulfonylamino)-7-chloro-9-methyl-2,3,4,5-tetrahydro-1-benzoxepine was obtained, m.p. 83–87° C.

EXAMPLE 12

5-(N-Butyl-N-methylsulfonylamino)-7-chloro-9-methyl-2,3,4,5-tetrahydro-1-benzoxepine

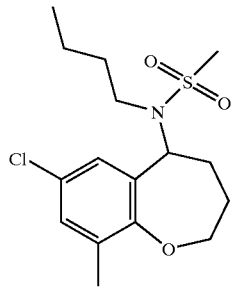

0.6 g of 5-amino-7-chloro-9-methyl-2,3,4,5-tetrahydro-1-benzoxepine (Example 10b) were reacted with methanesulfonyl chloride analogously to Example 10c. 0.6 g of 7-chloro-9-methyl-5-methylsulfonylamino-2,3,4,5-tetrahydro-1-benzoxepine was obtained, m.p. 154–156° C. By subsequent alkylation with butyl iodide analogously to Example 11, 0.6 g of 5-(N-butyl-N-methylsulfonylamino)-7-chloro-9-methyl-2,3,4,5-tetrahydro-1-benzoxepine was obtained, m.p. 106–110° C.

EXAMPLE 13

5-(N-Butyl-N-methylsulfonylamino)-7-nitro-2,3,4,5-tetrahydro-1-benzoxepine

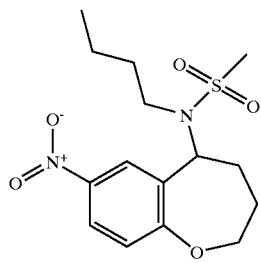

a) 10.0 g (61.7 mmol) of 3,4-dihydro-1-benzoxepin-5(2H)-one (*J. Chem. Soc., Perkin Trans.* 1 (1991), 2763) were introduced into 80 ml of conc. sulfuric acid with ice cooling. 5.77 g (67.9 mmol) of sodium nitrate were then added and the mixture was stirred for 90 min at 0° C. The reaction mixture was poured onto 800 ml of water, and the deposited product was filtered off with suction, washed until it was neutral and dried in vacuo. After recrystallization from isopropanol, 7 g of 3,4-dihydro-7-nitro-1-benzoxepin-5(2H)-one which was contaminated with about 12% of the corresponding 7,9-dinitro compound were obtained, m.p. 112–116° C. psb) 3.4 g (16.4 mmol) of 3,4-dihydro-7-nitro-1-benzoxepin-5(2H)-one were stirred for 3 h at 60° C. with 12.7 g (164 mmol) of ammonium acetate and 7.2 g (115 mmol) of sodium cyanoborohydride in 55 ml of methanol. After addition of 10 ml of water, the batch was concentrated in vacuo and the residue was taken up in EA and washed with dil. sodium hydroxide solution. The EA phase was extracted with dil. hydrochloric acid and the hydrochloric acid phase obtained was rendered alkaline with sodium hydroxide solution and extracted with EA. After drying the EA extract, 1.7 g of 5-amino-7-nitro-2,3,4,5-tetrahydro-1-benzoxepine were obtained. psc) From 1.6 g of 5-amino-7-nitro-2,3,4,5-tetrahydro-1-benzoxepine, 1.9 g of 5-methylsulfonylamino-7-nitro-2,3,4,5-tetrahydro-1-benzoxepine were obtained analogously to Example 8a, m.p. 150–15 1° C. psd) From 0.5 g of 5-methylsulfonylamino-7-nitro-2,3,4,5-tetrahydro-1-benzoxepine 0.6 g of 5-(N-butyl-N-methylsulfonylamino)-7-nitro-2,3,4,5-tetrahydro-1-benzoxepine were obtained by reaction with sodium hydride and iodobutane in DMF analogously to Example 11, m.p. 96–98° C.

EXAMPLE 14

7-Butoxy-3,4-dihydro-2H-1-benzoxepin-5-one

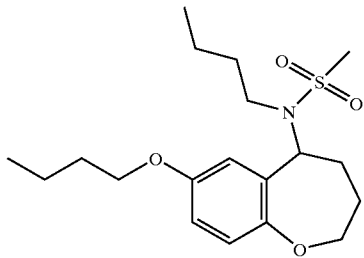

a) From 4-butoxyphenol, 7-butoxy-3,4-dihydro-2H-1-benzoxepin-5-one can be obtained by alkylation with ethyl 4-bromobutyrate, followed by hydrolysis and cyclization in the presence of polyphosphoric acid, as described in *J. Heterocyclic Chem.* 26 (1989), 1547 for the analogous 7-propoxy-3,4-dihydro-2H-1-benzoxepin-5-one. psb) From 7-butoxy-3,4-dihydro-2H-1-benzoxepin-5-one, 7-butoxy-3,4-dihydro-2H-1-benzoxepin-5-one can be obtained by reductive amination with ammonium acetate and sodium cyanoborohydride followed by reaction with methanesulfonyl chloride and finally alkylation with butyl iodide, as described in Example 13b–d.

EXAMPLE 15 trans-5-[N-(4-ethylphenyl)-sulfonylamino]-6,7,8,9-tetrahydro-5H-benzocycloheptene-6-ol

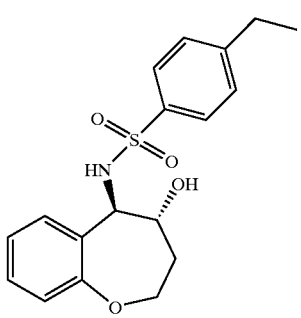

a) trans-5-Amino-6,7,8,9-tetrahydro-5H-benzocyclo hepten-6-ol
To a cold (0° C.) solution of 1-benzosuberone (7.83 g, 48.9 mmol) in methanol (90 ml) was added portionwise sodium borohydride (1.4 g, 36.8 mmol) over a 100 minute period. The mixture was stirred for a further 50 minutes at 0° C. Water (100 ml) was added. The white solid that resulted was filtered off, washed with water, and dried on a pump to give the corresponding alcohol (7.07 g, 89% yield).

A suspension of this compound (7.00 g, 43.2 mmol) and para-toluenesulfonic acid monohydrate (0.82 g, 4.3 mmol) in toluene (100 ml) was refluxed for 1 hour with the azeotropic removal of water. The resulting solution was diluted with ethyl acetate, then washed with saturated sodium hydrogen carbonate solution, dried over MgSO$_4$, filtered and evaporated to give 6,7-dihydro-5H-benzocycloheptene as a brown liquid (5.5 g, 88% yield).

To a cold (0° C.) solution of 6,7-dihydro-5H-benzocycloheptene (0.915 g, 6.35 mmol) in methylene chloride (20 ml) was added 75% meta-chloro-peroxybenzoic acid (1.75 g, 7.63 mmol). The reaction mixture was allowed to come to room temperature over an 18 hour period. The reaction mixture was diluted with methylene chloride and washed with saturated sodium hydrogen carbonate solution, dried over MgSO$_4$, filtered and evaporated to give the epoxide as a colorless oil (1.16 g, >100% yield, contaminated with meta-chlorobenzoic acid).

The crude epoxide was dissolved in 33% concentrated ammonia solution (50 ml) and allowed to stand at room temperature for 18 hours. The reaction mixture was then refluxed 90 minutes. The reaction mixture was cooled down. A white solid was collected and washed with water to yield a first lot of trans-5-amino-6,7,8,9-tetrahydro-5H-benzocyclo hepten-6-ol (0.18 g). The filtrate was evaporated. Flash chromatography (silica gel (10 g) CH$_2$Cl$_2$: MeOH; 9:1 to 4: 1) yielded a further quantity of the desired compound (0.30 g). The total yield of trans-5-amino-6,7,8, 9-tetrahydro-5H-benzocyclo hepten-6-ol was 0.48 g (42% yield from alkene).

b) trans-5-[N-(4-Ethylphenyl)-sulfonylamino]-6,7,8,9-tetrahydro-5H-benzocyclo hepten-6-ol To an ice-cold solution of trans-5-amino-6,7,8,9-tetrahydro-5H-benzocyclo hepten-6-ol (0.091 g, 0.514 mmol) in methylene chloride (20 ml) and triethylamine (1 ml) was added 4-ethyl benzene sulfonyl chloride (0.116 g, 0.566 mmol). The reaction mixture was stirred at 0° C. for 100 minutes, then at room temperature for 30 minutes. The reaction mixture was diluted with methylene chloride, then washed with 10% hydrochloric acid, saturated sodium hydrogen carbonate solution, dried over MgSO4, filtered and evaporated. Recrystallization from ethyl acetate/n-heptane yielded trans-5-[N-(4-ethylphenyl)-sulfonylamino]-6,7,8,9-tetrahydro-5H-benzocyclo hepten-6-ol as white crystals (0.11 g, 62% yield), m.p. 124–125° C.

EXAMPLE 16 trans-5-(N-Phenylsulfonylamino)-6,7,8,9-tetrahydro-5H-benzocyclohepten-6-ol

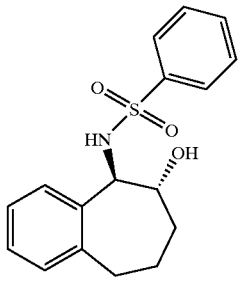

To an ice-cold solution of trans-5-amino-6,7,8,9-tetrahydro-5H-benzocyclo hepten-6-ol (0.056 g, 0.32 mmol; example 15 a) in methylene chloride (10 ml) and triethylamine (1 ml) was added 4-benzene sulfonyl chloride (0.056 g, 0.32 mmol). The reaction mixture was stirred at 0° C. then allowed to come to room temperature for 72 hours. The reaction mixture was diluted with methylene chloride, then washed with 10% hydrochloric acid, saturated potassium hydrogen carbonate solution, dried over MgSO$_4$, filtered and evaporated. Recrystallization from ethyl acetate/n-heptane yielded trans-5-(N-phenylsulfonylamino)-6,7,8,9-tetrahydro-5H-benzocyclo hepten-6-ol as white crystals (0.071 g, 71% yield), m.p. 128.0–128.2° C.

EXAMPLE 17 trans-5-[N-(4-Methylphenyl)-sulfonylamino]-6,7,8,9-tetrahydro-5H-benzocyclo hepten-6-ol

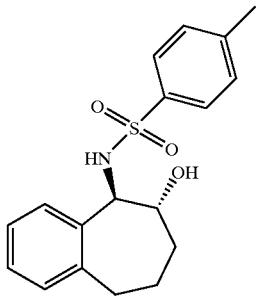

To an ice-cold solution of trans-5-amino-6,7,8,9-tetrahydro-5H-benzocyclo hepten-6-ol (0.046 g, 0.26 mmol; example 15 a) in methylene chloride (10 ml) and triethylamine (1 ml) was added 4-methylbenzene sulfonyl chloride (0.050 g, 0.26 mmol) The reaction mixture was stirred at 0° C. then allowed to come to room temperature for 72 hours. The reaction mixture was diluted with methylene chloride, then washed with 10% hydrochloric acid, saturated potassium hydrogen carbonate solution, dried over MgSO$_4$, filtered and evaporated. Recrystallization from ethyl acetate/n-heptane yielded trans-5-[N-(4-methylphenyl)-sulfonylamino]-6,7,8,9-tetrahydro-5H-benzocyclo hepten-6-ol as white crystals (0.063 g, 73% yield), m.p. 124.5–125.1° C.

EXAMPLE 18 trans-5-[N-(4-Methoxyphenyl)-sulfonylamino]-6,7,8,9-tetrahydro-5H-benzocyclohepten-6-ol

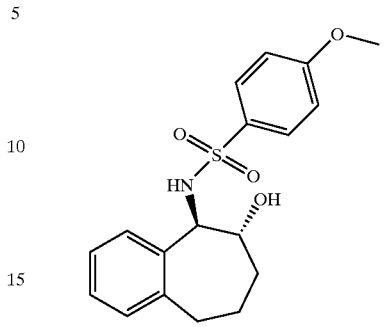

To an ice-cold solution of trans-5-amino-6,7,8,9-tetrahydro-5H-benzocyclo hepten-6-ol (0.038 g, 0.21 mmol; example 15 a) in methylene chloride (10 ml) and triethylamine (1ml) was added 4-methoxybenzene sulfonyl chloride (0.044 g, 0.21 mmol). The reaction mixture was stirred at 0° C. then allowed to come to room temperature for 72 hours. The reaction mixture was diluted with methylene chloride, then washed with 10% hydrochloric acid, saturated potassium hydrogen carbonate solution, dried over MgSO$_4$, filtered and evaporated. Recrystallization from ethyl acetate/n-heptane yielded trans-5-[N-(4-methoxyphenyl)-sulfonylamino]-6,7,8,9-tetrahydro-5H-benzocyclo hepten-6-ol as white crystals (0.063 g, 84% yield), m.p. 140–141° C.

EXAMPLE 19 trans-5-[N-(4-Chlorophenyl)-sulfonylamino]-6,7,8,9-tetrahydro-5H-benzocyclohepten-6-ol

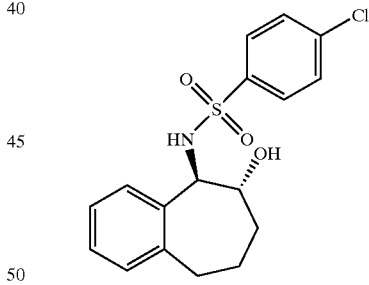

To an ice-cold solution of trans-5-amino-6,7,8,9-tetrahydro-5H-benzocyclo hepten-6-ol (0.050 g, 0.28 mmol; example 15a) in methylene chloride (10 ml) and triethylamine (1 ml) was added 4-chlorobenzene sulfonyl chloride (0.060 g, 0.28 mmol). The reaction mixture was stirred at 0° C. then allowed to come to room temperature for 72 hours. The reaction mixture was diluted with methylene chloride, then washed with 10% hydrochloric acid, saturated potassium hydrogen carbonate solution, dried over MgSO$_4$, filtered and evaporated. Recrystallization from ethyl acetate/n-heptane yielded trans-5-[N-(4-chlorophenyl)-sulfonylamino]-6,7,8,9-tetrahydro-5H-benzocyclo hepten-6-ol as white crystals (0.061 g, 62% yield), m.p. 172–173° C.

EXAMPLE 20 trans-5-[N-(4-Ethylphenyl)-sulfonylamino]-3-nitro-6,7,8,9-tetrahydro-5H-benzocyclohepten-6-ol The compound was synthesized via the following scheme:

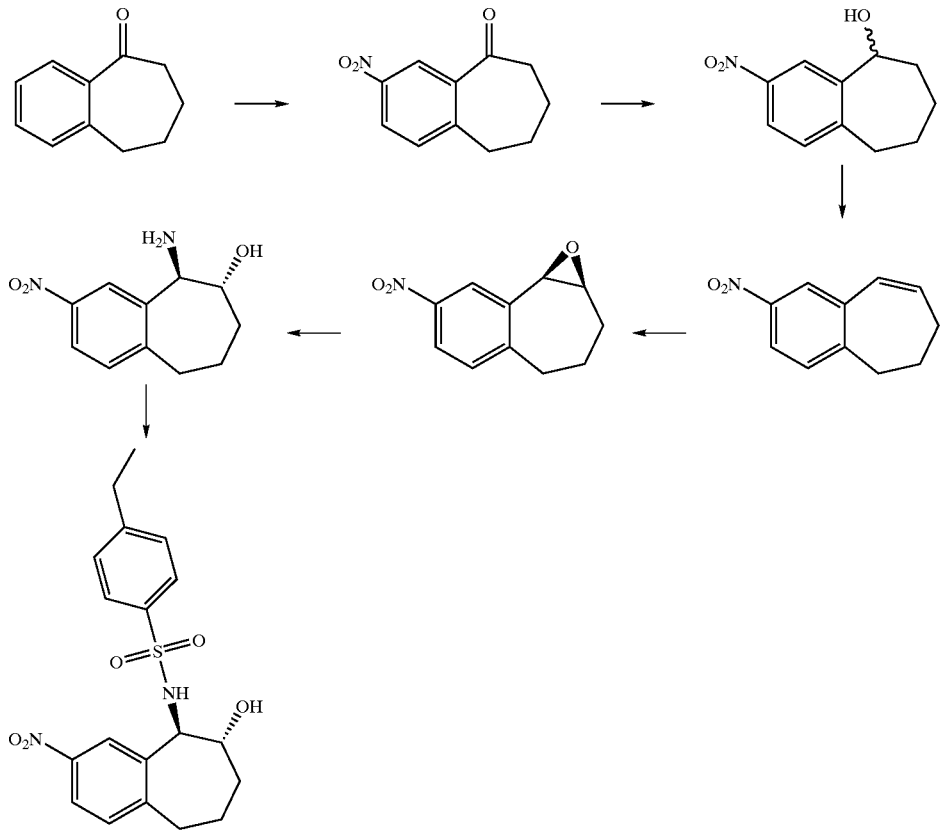

A solution of 3-nitro-6,7,8,9-tetrahydro-5H-benzocyclohepten-5-ol (1.00 g, 4.83 mmol; Smith and Berry, *J. Org. Chem.*, 1961, 26, 27) and para-toluenesulphonic acid monohydrate (0.40 g, 2.11 mmol) in toluene (250 ml) was refluxed for 5.5 hours, with the azeotropic removal of water. The resulting solution was diluted with ethyl acetate, then washed with saturated sodium hydrogencarbonate solution, dried over MgSO$_4$, filtered and evaporated to give the olefin as a brown liquid which crystallized on standing (0.85 g, 94% yield).

To a cold (0° C.) solution of this compound (0.539 g, 2.85 mmol) in methylene chloride (10 ml) was added 75% meta-chloro-peroxybenzoic acid (0.79 g, 4.56 mmol). The reaction mixture was allowed to come to room temperature over an 18 hour period. The reaction mixture was diluted with methylene chloride and washed with saturated potassium hydrogen carbonate solution. Dried over MgSO$_4$, filtered and evaporated to give the epoxide as a yellow solid (0.547 g, 94% yield).

The epoxide (0.547 g, 2.67 mmol) was suspended in 33% concentrated ammonia solution (20 ml). The reaction mixture was then refluxed 90 minutes during which time the reaction mixture became a solution, then a solid precipitated. Flash chromatography (methylene chloride: methanol; 99:1 to 4:1) gave trans-5-amino-3-nitro-6,7,8,9-tetrahydro-5H-benzocyclo hepten-6-ol as a white solid (0.290 g, 50%), m.p.=158–159.

To an ice-cold solution of trans-5-amino-3-nitro-6,7,8,9-tetrahydro-5H-benzocyclohepten-6-ol (0.196 g, 0.88 mmol) in methylene chloride (10 ml) and triethylamine (1 ml) was added 4-ethylbenzene sulfonyl chloride (0.181 g, 0.88 mmol). The reaction mixture was stirred at 0° C., then allowed to come to room temperature for 36 hours. The reaction mixture was diluted with methylene chloride, then washed with 10% hydrochloric acid, saturated potassium hydrogen carbonate solution, dried over MgSO$_4$, filtered and evaporated. Recrystallization from ethyl acetate/n-heptane yielded pure crystals of trans-5-[N-(4-ethylphenyl)-sulfonylamino]-3-nitro-6,7,8,9-tetrahydro-5H-benzocyclohepten-6-ol (0.181 g, 53% yield), m.p. 159–161° C.

EXAMPLE 21 trans-N-[9-(4-Ethyl-benzenesulfonylamino)-8-hydroxy-6,7,8,9-tetrahydro-5H-benzocyclohepten-2-yl]-3-methoxy-benzamide

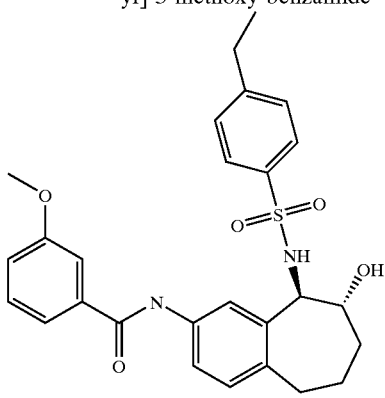

To a solution of trans-5-[N-(4-ethylphenyl)-sulfonylamino]-3-nitro-6,7,8,9-tetrahydro-5H-benzocyclo hepten-6-ol (0.085 g, 0.22 mmol; example 20) in ethanol (10 ml) was added 15 wt % titanium trichloride solution (2 ml, 2 mmol). After 2 hours the solvent was evaporated. The residue was dissolved in water and washed 3 times with methylene chloride. The aqueous phase was basified with saturated potassium hydrogen carbonate solution and extracted with methylene chloride. The organic phase was dried over $MgSO_4$, filtered and evaporated to give the corresponding amino compound (0.047 g, 60% yield).

To an ice-cold solution of the crude amine (0.046 g, 0.13 mmol) in methylene chloride (10 ml) and triethylamine (1 ml) was added 3-methoxybenzoyl chloride (0.024 g, 0.14 mmol). The reaction mixture was stirred at 0° C. then allowed to come to room temperature for 36 hours. The reaction mixture was diluted with methylene chloride, then washed with 10% hydrochloric acid, saturated potassium hydrogen carbonate solution, dried over $MgSO_4$, filtered and evaporated. Flash chromatography (silica gel (18 g) methylene chloride: methanol; 9:1) gave two compounds. The residue from the more polar compound was diluted in ethyl acetate and precipitated with n-heptane to yield the desired trans-N-[9-(4-ethyl-benzenesulfonylamino)-8-hydroxy-6,7, 8,9-tetrahydro-5H-benzocyclo hepten-2-yl]-3-methoxy-benzamide (0.018 g, 29% yield). MS (ES+) m/z=495 ((M+ H)$^+$, 100% rel. intensity).

The residue from the less polar compound was dissolved in ethyl acetate and precipitated with n-heptane to yield (+,−)-trans-3-methoxy-benzoic acid-5-(4-ethyl-benzenesulfonylamino)-3-(3-methoxy-benzoylamino)-6,7, 8,9-tetrahydro-5H-benzocyclo hepten-6-yl ester (0.011 g, 19% yield) MS (ES+) m/z=629 ((M+H)+, 70% rel. intensity).

Pharmacological Investigations $I_{sK}$ channels from man, rat or guinea-pig were expressed in *Xenopus* oocytes. To do this, oocytes were first isolated from *Xenopus laevis* and defolliculated. $I_{sK}$-encoding RNA synthesized in vitro was then injected into these oocytes. After $I_{sK}$ protein expression for 2–8 days, $I_{sK}$ currents were measured in the oocytes using the two microelectrode voltage clamp technique. The $I_{sK}$ channels were in this case as a rule activated using voltage jumps to −10 mV lasting 15 s. The bath was irrigated with a solution of the following composition: NaCl 96 mM, KCl 2 mM, $CaCl_2$ 1.8 mM, $MgCl_2$ 1 mM, HEPES 5 mM (titrated with NaOH to pH 7.5). These experiments were carried out at room temperature. The following were employed for acquiring data and analysis: Geneclamp amplifier (Axon Instruments, Foster City, USA) and MacLab D/A converter and software (ADInstruments, Castle Hill, Australia). The substances according to the invention were tested by adding them to the bath solution in different concentrations. The effects of the substances were calculated as the percentage inhibition of the $I_{sK}$ control current, which was obtained when no substance was added to the solution. The data were then extrapolated using the Hill equation in order to determine the inhibitory concentrations $IC_{50}$ for the respective substances.

For the compound of Example 13, an $IC_{50}$ value of 3.3 µmol/L was determined in the manner described.

References

A. E. Busch, H.-G. Kopp, S. Waldegger, I. Samarzija, H. S üβbrich, G. Raber, K. Kunzelmann, J. P. Ruppersberg and F. Lang; "Inhibition of Both Exogenously Expressed $I_{sK}$ and Endogenous K$^+$ Channels in *Xenopus* Oocytes by Isosorbide Dinitrate"; *J. Physiol.* 491 (1995), 735–741;

T. Takumi, H. Ohkubo and S. Nakanishi; "Cloning of a Membrane Protein That Induces a Slow Voltage-gated Potassium Current"; *Science* 242 (1989), 1042–1045;

M. D. Vamum, A. E. Busch, C. T. Bond, J. Maylie and J. P. Adelman; "The MinK Channel Underlies the Cardiac Potassium Current and Mediates Species-Specific Responses to Protein Kinase"; *Proc. Natl. Acad. Sci. USA* 90 (1993), 11528–115532.

What is claimed:

1. A compound according to formula I,

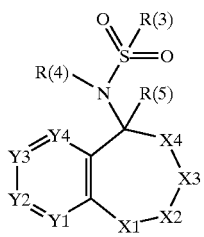

in which:
X1 is —$CH_2$—;
X2 is —CR(1)R(2)-,
R(1) and R(2) each independently represent hydrogen or alkyl having 1, 2 or 3 carbon atoms;
X3 is —$CH_2$— or —$C(CH_3)_2$—;
X4 is —$CH_2$— or —CHOH—;
Y1, Y2, Y3 and Y4 each independently represent —CR(12)-;
the radicals R(12) each independently represent hydrogen, F, Cl, Br, alkyl having 1, 2 or 3 carbon atoms, CN, $CF_3$, $NO_2$, or -Z-$C_mH_{2m}$—R(13);
Z is —O—, —CO—, —CO—O—, —OCO—, —S—, —SO—, —$SO_2$—, —$SO_2$NR(14)-, —NR(14)- or —CONR(14)-;
R(14) is hydrogen or alkyl having 1, 2 or 3 carbon atoms;
m is zero, 1, 2 or 3;
R(13) is hydrogen, $CF_3$, —NR(15)R(16), phenyl, thienyl, or an N-containing heterocycle having 1, 2, 3, 4, 5, 6, 7, 8 or 9 carbon atoms, where the N-containing heterocycle is pyridyl, imidazolyl, 1-piperidyl, 1-pyrrolidinyl, 4-morpholinyl, or 4-methylpiperizin-1-yl;
R(15) and R(16) each independently represent hydrogen or alkyl having 1, 2 or 3 carbon atoms;
R(3) is R(17)-$C_xH_{2x}$—;
R(17) is methyl;
x is zero, 1, 2 or 3;
R(4) is —$C_rH_{2r}$—R(20), where a $CH_2$ group of the group $C_rH_{2r}$ can be replaced by —O—, —CO—O—, —O—CC)—, —NR(21)- or —CONR(21)-;
R(21) is hydrogen or alkyl having 1, 2 or 3 carbon atoms;
r is zero, 1, 2, 3, 4, 5 or 6;
R(20) is methyl, $CF_3$ or pyridyl; and
R(5) is hydrogen;

or a stereoisomeric form or a mixture of stereoisomers thereof in any ratio, or a physiologically tolerable salt thereof.

2. A pharmaceutical composition, comprising an affective amount of at least one compound according to claim 1, together with a pharmaceutically acceptable carrier.

3. A method for treating K$^+$ channel-mediated illness in a host, comprising administering to the host in need thereof an affective amount of a compound according to claim 1.

4. A method for inhibiting gastric acid secretion in a host, comprising administering to the host in need thereof an affective amount of a compound according to claim 1.

5. A method for treating ulcers of the stomach or of the intestinal region in a host, comprising administering to the host in need thereof an affective amount of a compound according to claim 1.

6. A method for treating reflux esophagitis in a host, comprising administering to the host in need thereof an affective amount of a compound according to claim 1.

7. A method for treating diarrheal disorder in a host, comprising administering to the host in need thereof an affective amount of a compound according to claim 1.

8. A method for treating arrhythmia in a host, comprising administering to the host in need thereof an affective amount of a compound according to claim 1.

9. A method of claim 8, wherein the arrhythmia is a trial, ventricular or supraventricular.

10. A method for treating cardiac arrhythmias which can be eliminated by action potential prolongation in a host, comprising administering to the host in need thereof an affective amount of a compound according to claim 1.

11. A method for treating atrial fibrillation or atrial flutter in a host, comprising administering to the host in need thereof an affective amount of a compound according to claim 1.

12. A method for treating reentry arrhythmias in a host comprising administering to the boat in need thereof an affective amount of a compound according to claim 1.

13. A method for preventing sudden heart death as a result of ventricular fibrillation in a host, comprising administering to the host in need thereof an affective amount of a compound according to claim 1.

14. A method for treating cardiac insufficiency in a host, comprising administering to the host in need thereof an affective amount of a compound according to claim 1.

* * * * *